(12) United States Patent
Zhang et al.

(10) Patent No.: US 11,726,049 B2
(45) Date of Patent: Aug. 15, 2023

(54) SMALL ANGLE X-RAY SCATTERING METHODS FOR CHARACTERIZING THE IRON CORE OF IRON CARBOHYDRATE COLLOID DRUG PRODUCTS

(71) Applicant: Amphastar Pharmaceuticals, inc., Rancho Cucamonga, CA (US)

(72) Inventors: Jack Yongfeng Zhang, Diamond Bar, CA (US); Mary Zi-Ping Luo, Diamond Bar, CA (US); Thang Kien Chiu, Rancho Cucamonga, CA (US); Anthony Marrs, Costa Mesa, CA (US); Selina Su, South El Monte, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 17/921,235

(22) PCT Filed: May 4, 2021

(86) PCT No.: PCT/US2021/030657
§ 371 (c)(1),
(2) Date: Oct. 25, 2022

(87) PCT Pub. No.: WO2021/226087
PCT Pub. Date: Nov. 11, 2021

(65) Prior Publication Data
US 2023/0124114 A1    Apr. 20, 2023

Related U.S. Application Data

(60) Provisional application No. 63/019,864, filed on May 4, 2020.

(51) Int. Cl.
*G01N 23/201* (2018.01)
*G01N 15/02* (2006.01)
(Continued)

(52) U.S. Cl.
CPC ........... *G01N 23/201* (2013.01); *G01N 15/02* (2013.01); *G01N 23/207* (2013.01); *G01N 33/15* (2013.01);
(Continued)

(58) Field of Classification Search
CPC .... G01N 23/201; G01N 15/02; G01N 23/207; G01N 33/15; G01N 2223/504; G01N 2223/056; G01N 2223/60
See application file for complete search history.

(56) References Cited

U.S. PATENT DOCUMENTS 10,478,450 B2 * 11/2019 Helenek .................. A61P 35/00
2009/0202815 A1 * 8/2009 Campazzi ............... C09D 5/084
106/14.44

FOREIGN PATENT DOCUMENTS

WO    WO-2018102681 A1 *  6/2018  ............. G01N 24/08

OTHER PUBLICATIONS

Socoliuc et al., "Magnetic Nanoparticle Systems for Nanomedicine—a Materials Science Perspective," MagnetoChemistry, vol. 6, No. 1, Jan. 2020, 1-36.

(Continued)

*Primary Examiner* — David P Porta
*Assistant Examiner* — Mamadou Faye
(74) *Attorney, Agent, or Firm* — IceMiller LLP

(57) ABSTRACT

The present disclosure introduces methods for characterizing iron core carbohydrate colloid drug products, such as iron sucrose drug products. Disclosed methods enable the characterization of the iron core size of the iron core nanoparticles in iron carbohydrates as they exist in the formulation in solution, such as e.g. iron sucrose drug products, and more particularly, the average particle diameter size and size distribution(s) of the iron core nanoparticles. The disclosed methods apply small-angle X-ray scat- (Continued)

tering (SAXS) in parallel beam transmission geometry, with a sample mounted inside a capillary and centered in the X-ray beam, to iron carbohydrates, such as iron sucrose, in solution without the need to modify the sample, such as to remove unbound carbohydrates, dilute, or dry the sample, to accurately characterize the average iron core particle diameter size of the iron core nanoparticles. An example application of the disclosed method is to perform SAXS measurements under identical instrument settings on two samples of the same type of iron core nanoparticle colloid drug product for the purpose of comparing their iron core structures. Such comparisons are typically performed during the iron core carbohydrate colloid drug development process, and can include comparisons of samples that have been manipulated.

24 Claims, 11 Drawing Sheets

(51) Int. Cl.
  *G01N 23/207* (2018.01)
  *G01N 33/15* (2006.01)

(52) U.S. Cl.
  CPC .. *G01N 2223/054* (2013.01); *G01N 2223/056* (2013.01); *G01N 2223/60* (2013.01)

(56) References Cited

OTHER PUBLICATIONS

Thunemann et al., "In Situ Analysis of a Bimodal Size Distribution of Superparamagnetic Nanoparticles," Analytical Chemistr, Jan. 2009, vol. 81, 296-301.
Gilbert et al., "Stable cluster formation in aqueous suspensions of iron oxyhydroxide nanoparticles," Journal of Colloid and Interface Science, vol. 313, No. 1, Sep. 2007, 152-159.
Huang et al., "Enhancement of Curcumin water dispersibility and antioxidant activity using core-shell protein-polysaccharide nanoparticles," Food Research International, vol. 87, Jun. 2016, 1-9.
International Search Report and Written Opinion for PCT/US2021/03065/, dated Jul. 30, 2021.

\* cited by examiner

SMALL ANGLE X-RAY SCATTERING METHODS FOR CHARACTERIZING THE IRON CORE OF IRON CARBOHYDRATE COLLOID DRUG PRODUCTS

CROSS-REFERENCE TO RELATED APPLICATIONS

This application is a National Stage Application of International Patent Application No. PCT/US2021/030657, filed May 4, 2021, which claims priority to U.S. Provisional Patent Application No. 63/019,867 (filed May 4, 2020), the disclosure of which are incorporated by reference in their entireties.

TECHNICAL FIELD

The present disclosure generally pertains to methods for characterizing iron core in iron carbohydrate colloid complexes, such as e.g. iron sucrose, including iron sucrose drug products, using small-angle X-ray scattering.

BACKGROUND

Iron sucrose is clinically indicated for the treatment of iron deficiency anemia, such as iron deficiency anemia in patients with chronic kidney disease (CKD). Some iron sucrose drug products are injectable solutions for intravenous injection. Iron sucrose exhibits a colloidal system in the lower nanometer size range in which an iron core (e.g. ferric hydroxide) is surrounded by a carbohydrate shell (e.g. sucrose shell). The iron core can be made of iron salt or iron oxyhydroxide nanoparticles. The carbohydrate shell serves to reduce the release of the bioactive iron and maintain the resulting particle in the colloidal system.

An iron sucrose injectable solution (e.g. single-use vials) is an example of an iron sucrose drug product currently available to patients. An iron sucrose injectable solution is a sterile, colloidal solution of polynuclear iron (III)-hydroxide (e.g. ferric hydroxide) in complex with sucrose. In iron sucrose, sucrose plays the role of ligands in the core of iron-(III) hydroxide. Iron sucrose injection has a molecular weight of about 34,000 to 60,000 Daltons and a molecular formula of:

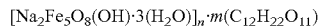

where n is the degree of iron polymerization and m is the number of sucrose particles associated with the iron-(III) hydroxide. For example, there can be as many as 50 (or more) sucrose particles associated with a single iron-(III) hydroxide. An example of an iron sucrose injectable drug product is Venofer®, having an equivalent concentration of 20 mg/mL of elemental iron. Venofer® is an example of a comparison product for iron sucrose.

Following intravenous administration, the iron sucrose drug product dissociates into iron and sucrose and the iron is transported as a complex with transferrin to target cells such as erythroid precursor cells. The iron in the precursor cells is incorporated into hemoglobin as the cells mature into red blood cells.

In iron sucrose and other iron carbohydrate colloid drug products, the iron core size is structurally similar and heavily dependent on the physiochemical properties of the carbohydrate component, such as the length of the carbohydrate chain, degree of branching of the chains, and identity and structure of the smallest glycosidic unit. Therefore, it is essential to have an accurate and reliable method for determining the effect of the carbohydrate component on the property of the iron core, such as the size of the iron core, wherein the result of such method is not affected by differences in sample preparation and method specificity (i.e., the same results is obtained by different investigators if the same technology is used). However, it is a technical challenge to characterize the iron core size because of the colloidal structure of iron sucrose and other iron core carbohydrate drug products, and the nanometer (nm) size range.

In iron sucrose, for example, the colloidal structure of an iron core is surrounded by as many as 50 sucrose particles. The sucrose particles act as a ligand and surround the iron core, which renders certain routine particle size characterization methods ineffective in characterizing the iron core size. For example, light scattering is a known particle size characterization method but because of iron sucrose's colloidal structure and the plurality of sucrose particles surrounding the iron core, light scattering cannot characterize the iron core size. Instead, light scattering can only characterize the iron sucrose particle as a whole. In addition, atomic force microscopy is another known particle size characterization method but is also disadvantaged when characterizing the iron core size because it cannot produce stable results due to large fluctuations.

Another technical challenge is due to the small size of the iron carbohydrate complex (e.g., nanometer size range). In iron sucrose, the iron core generally has a particle diameter in a range of about 2 nm to about 5 nm, and the iron sucrose particle generally has a particle diameter in a range of about 8 nm to about 10 nm. In addition, there can be as many as 50 sucrose nanoparticles surrounding the iron core nanoparticle. Therefore, due to the closeness in the nm size range between the iron core and the iron sucrose, it is a technical challenge to accurately characterize the iron core size. Other iron carbohydrate colloid drug products have similar complicating features of iron sucrose (e.g., nanometer size, closeness of size of the iron core and whole iron carbohydrate nanoparticle, and heterogeneity of the number of carbohydrate molecules surrounding the iron core).

Needed in the art is a robust method to accurately characterize the iron core size of iron carbohydrate complexes, including iron sucrose. Accordingly, the present invention solves these technical challenges by presenting methods to characterize the iron core size in iron carbohydrate complexes, including iron sucrose drug products. Although they have been used to characterize iron carbohydrate colloid nanoparticles, there are severe limitations to current physiochemical methods that make them not suitable and/or reliable for accurately determining the property of the iron core, such as the size of just the iron core, and/or of iron core carbohydrate nanoparticles as they exist in colloid solutions.

In gel-permeation chromatography (GPC), molecules are filtrated based on their overall size and conformation. However, the molecules can also interact with the gel-filtration resin, and gel filtration parameters such as the concentration of the molecules, temperature, filtration speed, and filtration buffer type. Each of these variables can affect the estimation of the particle size and size distribution. Thus, the results of GPC-based size determination are affected by the specifics of the experimental conditions, and although GPC has been used to characterize the size and size distribution of iron core carbohydrate colloid nanoparticles, including that of iron sucrose, the size and size distribution determined are that for the overall nanoparticle, which includes the bound carbohydrate shell, and not that of the iron core itself.

In dynamic light scattering (DLS), the degree to which light is scattered depends on: (a) the tumbling property of the nanoparticle, which is affected by experimental conditions such as the existence of free carbohydrates; (b) particle density, which may affect iron core stability; and (c) the physiochemical property of the scattering medium. Importantly, removal of free, unbound carbohydrates by dialysis or centrifugation may affect iron core stability, and, therefore, the particle size and size distribution need to be measured with and without removal of free carbohydrates. Thus, the results of DLS-based size determination are affected by the specifics of the experimental conditions, and although DLS has been used to characterize the size and size distribution of iron core carbohydrate colloid nanoparticles, including that of iron sucrose, the size and size distribution determined are that for the overall nanoparticle, which includes the bound carbohydrate shell, and not that of the iron core itself.

Although there are existing physical methods currently used for determining the size of the iron core itself, such as powder X-ray diffraction (PXRD), atomic force microscopy (AFM), and cryogenic transmission electron microscopy (cryo-TEM), the results of these determinations are again heavily affected by the specifics of the methods, such as instrument variability, instrument parameters, data analysis methodology, and most importantly, all these methods require time-consuming and extensive manipulations of the sample in order for the technology to work, thereby potentially perturbing the iron core. In addition, the discrete nature of these methods—a few peaks in PXRD, and only a few hundred or a few thousand particle counts in AFM and cryo-TEM—generally does not readily allow one to determine particle size distributions, let alone one that is accurate.

In powder X-ray diffraction (PXRD) of iron carbohydrate colloid drug products, there are two major limitations that make the method not reliable for iron core size determination: (1) the colloid solution must be first dried and ground to a fine powder, which results in an amorphous powder and can potentially perterb the iron core; and (2) one must make the basic assumption that the one or two amorphous peaks observed in the diffraction pattern of the freeze-dried powder, that happen to overlap one of several well-defined peaks in crystalline powders of diffraction standards such as Magnetite, Ferrihydrite and Akaganeite, means the iron core has the same structure as the crystalline standards. For example, M R Jahn et al. (*Eu. J. Pharma. and Biopharma.* 2011, vol. 78, p. 480-491) measured the iron core size of 3-4 nm for various iron core carbohydrates with this method using this assumption.

In atomic force microscopy (AFM) of iron carbohydrate colloid drug products, unbound carbohydrate molecules must be removed, and the samples diluted for optimal imaging, which again may perturb the core structure. Importantly, one skilled in the art of AFM knows that both morphology and measurement of lateral diameters are heavily affected by sample dilution, and the specifics of the AFM measurement, such as the shape of the probe and the scan mode.

In cryogenic transmission electron microscopy (cryo-TEM) of iron carbohydrate colloid drug products, to optimize image contrast so that the electron-dense iron core can be differentially imaged, the unbound carbohydrate molecules must also be removed from the iron core carbohydrate colloid product, which again may perturb the core structure. In addition, to reduce particle crowding in the images, as overcrowding leads to over estimation of the particle size, the sample must be diluted several fold, which may affect core stability, and therefore, the effect of dilution on the iron core structure must be investigated. Importantly, one skilled in the art of cryo-TEM knows that the size determined is highly dependent on the thresholds of the particle filtering parameters used for particle analysis, with lower thresholds resulting in more noise that results in over estimation of the particle size (e.g., more particles appear overlapped and are counted together), and higher thresholds resulting in less noise and smaller particle boundaries that results in under estimation of the particle size. Thus, the result of the determination is strongly biased by the specifics of the sample preparation, imaging protocol, and imaging analysis details selected by the investigator.

Nevertheless, using AFM and cryo-TEM methods which required the extensive sample manipulations discussed above, the iron core of iron sucrose was measured to have a particle size of 2.5±1.4 nm and 1.8±0.6 nm by AFM and cryo-TEM, respectively (data not shown). These values using two different techniques are approximately the same as the samples were processed approximately the same way, but are approximately half the value of 5.0±0.8 nm obtained by M R Jahn et al. (*Eur. J. Pharm. and Biopharm.*, 2011, vol. 78, p. 480-491) using cryo-TEM, which is possibly due to different sample processing, imaging protocol, and/or imaging analysis parameters.

Thus, what is needed is are new methods of characterizing the iron core of iron carbohydrate colloid drug products that overcome at least the limitations of PXRD, AFM and cryo-TEM cited above.

SUMMARY

Exemplary embodiments of the present invention address at least the above problems and/or disadvantages and advance the art by providing at least the features described below. Additional objects, advantages, and salient features of exemplary embodiments of the present invention will become apparent to those skilled in the art from the following detailed description, which, taken in conjunction with the annexed drawings, discloses exemplary embodiments of the present invention.

The disclosure provides for methods of characterizing an average particle diameter size of iron core nanoparticles in an iron carbohydrate drug product (such as e.g. iron sucrose) using small-angle X-ray scattering (SAXS).

One embodiment of the invention is a method for characterizing an average particle diameter size and size distribution(s) of iron core nanoparticles in an iron carbohydrate drug product which comprises the steps of: (1) configuring an X-ray diffractometer, such as a powder X-ray diffractometer, in a parallel beam transmission geometry, and a capillary mount for the sample, for small-angle X-ray scattering (SAXS); (2) performing SAXS data collection on a first sample having a plurality of iron carbohydrate particles to generate a first SAXS data, wherein the SAXS data includes intensity counts as a function of scattering angle, wherein each iron carbohydrate particle exhibits a colloidal system comprising an iron core nanoparticle and a plurality of carbohydrate nanoparticles surrounding the iron core nanoparticle, and wherein the SAXS is performed over a pre-determined range of scattering angles; (3) performing SAXS over the pre-determined range of scattering angles with identical instrument settings as the first sample on a second sample comprising the same or approximately the same composition as the first sample, but without iron, to generate a second SAXS data; (4) generating a background-subtracted SAXS data by subtracting the second SAXS data from the first SAXS data, wherein the background-subtracted SAXS data includes background-subtracted intensity counts as a function of scattering angle; (5) generating a modeled background-subtracted SAXS data by modeling the background-subtracted SAXS data using a projected shape of the iron core nanoparticle and a projected particle diameter size of the iron core nanoparticle; generating a particle size distribution data based on the modeled background-subtracted SAXS data, wherein the distribution data is a Gamma or Lognormal distribution as a function of particle diameter size of the iron core nanoparticle; outputting the size distribution, average particle diameter and relative size distribution; and (6) determining the average particle diameter size and other particle size parameters of the iron core nanoparticles from the particle size distribution(s). In some embodiments of the methods, the step of configuring an X-ray diffractometer, such as a powder X-ray diffractometer, in a parallel beam transmission geometry, and a capillary mount for the sample, for small-angle X-ray scattering (SAXS) may be optional or may be omitted.

In certain embodiments, the iron carbohydrate colloid drug product is iron sucrose, a high molecule weight iron dextran drug product, a low molecular weight iron dextran drug product, a sodium ferric gluconate drug product, an iron carboxymaltose drug product, or a ferumoxytol drug product. In certain embodiments, the particle size distribution are number-averaged or volume-averaged.

In certain embodiments, separate SAXS data are collected, using the same instrument settings as the background sample, on two or more separate samples of the same type of iron core carbohydrate colloid drug, their background-subtracted X-ray intensities separately modelled with identical modelling parameters, their separate particle size distributions outputted, and the calculated averaged particle diameter and other size parameters for the iron core nanoparticles compared with each other.

In certain embodiments, the projected shape of the iron core particle is a solid sphere, a solid spheroid, a solid cylinder, or a Debye particle of undefined shape. When there is separate evidence that a particular iron core carbohydrate has a non-solid iron core structure, a core shell model for the iron core can also be used.

In certain embodiments, the particle sizes can be modelled as two or more separate populations of sizes, each population characterized by its own average particle diameter, relative size distribution value, and distribution data. As illustrated by Examples 5 and 6, suitable pre-determined range of scattering angles include but are not limited to: a range, in 2-theta (2Θ), from about 0.1 degrees to about 8 degrees; a range, in 2-theta (2Θ), from about 0.1 degrees to about 5 degrees; a range, in 2-theta (2Θ), from about 0.2 degrees to about 8 degrees; or a range, in 2-theta (2Θ), from about 0.2 degrees to about 5 degrees.

In certain embodiments, the modelling of the X-ray intensities is performed without background subtraction. This can be used, for example, when the density of the iron core of a novel iron carbohydrate colloid drug is significantly more dense than currently observed that the diffraction intensity of the buffer solution comprising the same or approximately the same composition as the drug but without iron is insignificant by comparison; or when the composition of the carbohydrate or other non-iron components of the drug product are unknown.

The current invention has the advantage that the SAXS data is performed on un-manipulated samples of the iron core carbohydrate colloid drug product as they exist in solution. However, the investigator is not precluded from manipulating the drug product first, such as by sample dilution, if that is desired as part of product development.

The disclosure also includes instruments such as point-collimation instrument or line-collimation instrument configured to perform the methods of the invention. The disclosure also includes a computer program product on a non-transitory computer readable medium and having code adapted to be executed by a computer to perform the methods of the invention.

BRIEF DESCRIPTION OF THE FIGURES

The above and other exemplary features and advantages of certain exemplary embodiments of the present invention will become more apparent from the following description of certain exemplary embodiments thereof when taken in conjunction with the accompanying drawings in which:

FIG. 1 shows the Raw X-ray intensity.

FIG. 2 shows the simulated X-ray intensity.

FIG. 5 shows a Ydx plot of the cumulative sum of (distribution*step-size).

FIG. 6A shows the effect of 2Θ end angle on particle size estimation. FIG. 6B shows the percent deviation from value obtained using full data range.

FIG. 7A shows the effect of 2Θ start angle on particle size estimation. FIG. 7B shows the percent deviation from value obtained using full data range.

FIG. 10 shows the effect of background subtraction as a XYdx plot.

FIG. 11 shows the effect of background subtraction as a Ydx plot.

Table 1 in the Examples below shows the legend for FIGS. 1-5. Throughout the drawings, like reference numerals will be understood to refer to like elements, features, and structures.

DETAILED DESCRIPTION

Figure 1:
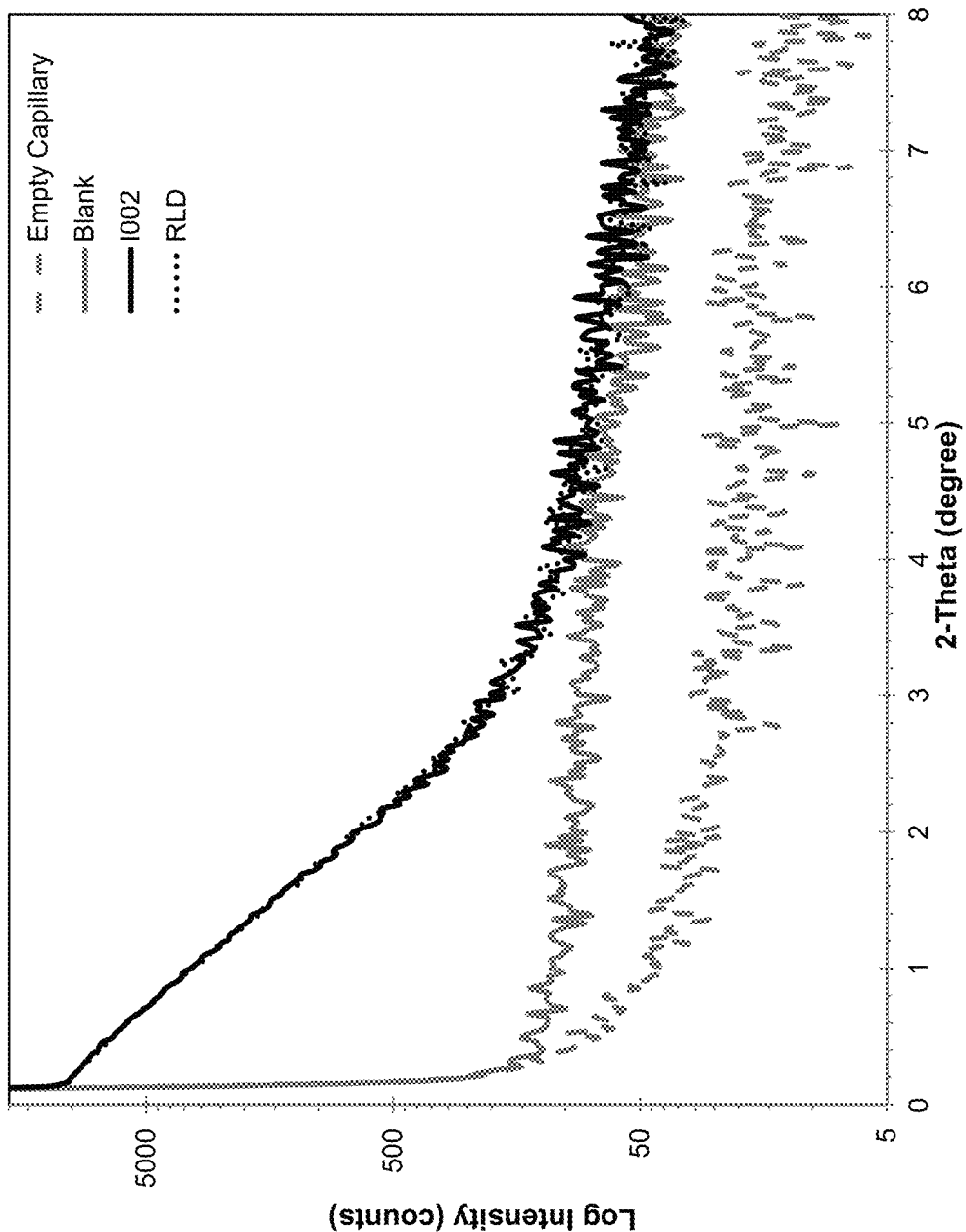
FIG. 1 is a graph showing the scattering intensity data from the performed SAXS on an exemplary iron sucrose drug product.

The matters exemplified in this description are provided to assist in a comprehensive understanding of exemplary embodiments of the invention with reference to the accompanying drawing figures. While the subject matter of the present disclosure has been described in connection with certain embodiments, it is to be understood that the present disclosure is not limited to the disclosed embodiments, but, on the contrary, is intended to cover various modifications and equivalent arrangements included within the spirit and scope of the appended claims, and equivalents thereof. Accordingly, those of ordinary skill in the art will recognize that various changes and modifications of the exemplary embodiments described herein can be made without departing from the scope and spirit of the present disclosure.

This disclosure provides new methods of characterizing the iron core of iron carbohydrate drug product, which overcome at least the limitations of PXRD, AFM, and cryo-TEM cited above, and can be used to accurately determine the size and size distribution of the iron core of iron carbohydrate colloid products, and importantly, as they exist in solution that (a) does not require sample manipulation so that the iron core is un-perturbed, (b) does not require apriori information or assumption of the iron core's sub-structure, and (c) can be performed rapidly.

The methods combine the major benefits from different technologies: (1) differential scattering of X-rays by the electron-dense iron core, as in cryo-TEM, versus the carbohydrate component, which is transparent to X-rays (i.e., because the carbohydrate component comprises the light elements carbon, oxygen and hydrogen, and does not have crystalline order, it only contributes weak diffuse scattering of X-rays); (2) amplification of the diffraction signal, as in PXRD (colloidal iron carbohydrates in solution with 10-100 mg/mL of iron has a density of $1^{20}$-$1^{21}$ irons/mL; in AFM and cryo-TEM, the data sampling size is only a few hundred to a few thousand particles per image); and (3) small-angle X-ray scattering (SAXS), as in SAXS of protein macromolecules, or bio-SAXS, which requires a priori knowledge of the sub-structure for modeling to be possible.

It is important to note that only scattering of X-rays at low angles (hence, the term small-angle X-ray scattering, or SAXS) is measured because none of the components of colloidal iron core carbohydrate products has long-range crystalline order, and so there is no X-ray scattering signal at high angles, so they are not collected (i.e. having such long-range crystalline order would require high-angle X-ray scattering measurements of non-amorphous dried powders of the iron core carbohydrate compound, or single crystals thereof, both of which are not possible due to the colloidal nature of the iron core carbohydrate product).

In addition, whereas bio-SAXS of protein molecules, which comprises mostly of light elements carbon, oxygen, hydrogen, nitrogen, and sulfur, requires knowing the three dimensional single-crystal X-ray structure of the sub-structure beforehand, such as of the atomic structure of the individual protein subunits within the large protein complex, for the modeling to succeed, SAXS of iron carbohydrate colloid products does not require apriori knowledge of the sub-structure of the iron core. Again, this is because of the differential scattering of the electron-dense iron core versus the transparent carbohydrate component, and the low-angle scattering nature of the method.

In addition, the SAXS methods described herein have the additional advantage that they can be quickly performed using an in-house stand-alone X-ray diffractometer and does not require synchrotron radiation.

In certain embodiments, the SAXS methods described herein comprise the following steps: (1) configuring a commercially available X-ray powder diffractometer, such as the SmartLab SE from Rigaku Americas Inc., in parallel beam transmission geometry for SAXS; (2) diffracting a first sample of an un-manipulated iron carbohydrate colloid product as it exists in solution, mounted in a capillary, from diffraction angles of 2-theta of about 0.1 degree to 8 degree in 0.03 degree increments; (3) diffracting with the same instrument settings a second sample of a background buffer solution comprising the same or approximately the same carbohydrate composition as the first sample, but without iron; (4) subtracting the SAXS diffraction pattern of the second sample from the first; (5) generating a modeled background-subtracted SAXS data by modelling the background-subtracted X-ray intensities as a function of 2-theta angles as a Gamma or Lognormal distribution(s) of solid spheres, ellipsoids or cylinders of different sizes; and outputting the distribution(s), average particle diameter and relative size distribution; and (6) computing the volume-averaged or number-averaged particle diameter and other size parameters from the computed particle size distribution(s).

As presented in the Examples herein, this disclosure shows that the number-averaged average iron core diameter particle size of iron sucrose nanoparticle colloidal solution, when modeled as a single distribution of solid spheres of different sizes, is 2.6±1.3 nm, which closely matches the value 2.5±1.4 nm obtained by AFM. When volume-averaged, the corresponding iron core size was 4.6±1.7 nm.

Because the carbohydrate component of the iron carbohydrate colloid products only comprise the light elements of carbon, oxygen and hydrogen, has colloidal order and no long-range crystalline order, and thereby only exhibits very weak diffuse X-ray scattering, that the carbohydrate structure of the second sample need not exactly match that of the first sample. This means, for example, that a 5% w/v glucose solution can substitute for a 1% w/v dextran solution, where the dextran is made of pentamer of linked glucosides. Additionally, whereas the carbohydrate exists as nanoparticles when bound to the iron core in iron core carbohydrates, the carbohydrate in the second sample may be isolated carbohydrate molecules because the iron core is absent.

It is further noted that with these rapid SAXS methods for determining iron core particle size, one skilled in the art can use them to compare or determine the iron core size properties of different iron core carbohydrate formulations, or for further development of iron core carbohydrate products with a more stabilized iron core based on modifications of the carbohydrate moiety.

The disclosure is based on the discovery that it is possible to accurately determine the iron core particle size and particle size distribution of iron sucrose in solution as it exists in the formulation (e.g., the sample has not been manipulated by methods such as removal of unbound sucrose, sample dilution, or sample drying) by small-angle X-ray scattering (SAXS) using the unique methods disclosed herein. This is because whereas the electron-dense iron core strongly diffracts X-rays by SAXS, the sucrose shell surrounding the iron core and unbound sucrose in the medium are transparent to X-rays (i.e. X-rays only "see" the iron core while the carbohydrate component diffracts X-rays very weakly, with a diffuse scattering profile of water). The measured values are accurate as daily quality control SAXS measurements, using the same instrument setting yielded average particle size measurement values of 5.6±0.3 nm for a commercially available solution of 5 nm gold nanoparticles of average size, was 5±2 nm. In addition, the disclosure provides for unique methods of characterizing iron carbohydrate products using SAXS to enable accurate measuring of the iron core particle size and particle size distribution.

Via use of the methods of the invention, it is possible to accurately measure the iron core size of an iron carbohydrate product without having to manipulate the sample. Specifically, the methods of the invention allow for characterizing the iron core of iron carbohydrate colloid drug product without the need to modify the sample, such as to remove unbound carbohydrates, dilute, or dry the sample.

Accordingly, the disclosure provides methods for characterizing iron carbohydrates, such as iron sucrose drug products. The methods of the disclosure enable the characterization of the size of the iron core nanoparticles in iron carbohydrates, such as e.g. iron sucrose drug products, and more particularly, the average particle diameter of the iron core nanoparticles. The methods disclosed herein use small-angle X-ray scattering (SAXS) of iron carbohydrates, such as iron sucrose, to accurately characterize the average particle diameter size of the iron core nanoparticles.

The methods of the claimed invention also allow for identifying putative iron carbohydrate drug products that have similar iron core properties as determined by SAXS, such as in the examples disclosed comparing their iron core's particle shape, size distribution, relative size distribution, and size parameters such as average diameter and $D_x$ parameters, where $D_x$ is the average particle size at which x percent of the particles are smaller than or equal to that size.

I. Definitions

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments include the discussed feature, advantage, or mode of operation.

Unless otherwise defined herein, scientific, and technical terms used in connection with embodiments of present invention shall have the meanings that are commonly understood by those of ordinary skill in the art. Nomenclatures used in connection with, and techniques described herein are those known and commonly used in the art. Also, descriptions of well-known functions and constructions are omitted for clarity and conciseness.

Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

As used herein, the singular forms "a," "an," and "the" are intended to include the plural forms as well, unless the context clearly indicates otherwise. It will be further understood that the terms "comprises," "comprising," "includes," "including," "have" and/or "having" when used herein, specify the presence of stated features, integers, steps, operations, elements, and/or components, but do not preclude the presence or addition of one or more other features, integers, steps, operations, elements, components, and/or groups thereof.

As used herein, comparison products of carbohydrate colloid drug may be Venofer®, Dexferrum®, Cosmofer®, Ferrlecit®, Ferinject®, Injectafer®, or Feraheme®, or other iron carbohydrate colloid drug products with similar characteristics. The comparison products of carbohydrate colloid drug may an iron carbohydrate colloid drug product, which has received regulatory approval by, for example, the FDA, e.g. an approved drug.

As used herein, the term "SAXS" refers to small-angle X-ray scattering.

As used herein, the term "EEC" refers to equivalence evaluation criteria. The EEC can be determined using one or more of the following EEC Equations discussed below.

II. Iron Carbohydrate Complexes

The present disclosure introduces methods for characterizing iron carbohydrate complexes, such as iron sucrose drug products. Currently available iron sucrose drug products include iron sucrose injectable solutions, such as injectable solutions in single-use vials.

A. Iron Sucrose Drug Products

An iron sucrose injectable solution is a sterile, colloidal solution of polynuclear iron (III)-hydroxide (e.g. ferric hydroxide) in complex with sucrose. Iron sucrose injection has a molecular weight of about 34,000 to 60,000 Daltons and a molecular formula of:

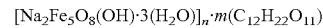

$$[Na_2Fe_5O_8(OH) \cdot 3(H_2O)]_n \cdot m(C_{12}H_{22}O_{11})$$

where n is the degree of iron polymerization and m is the number of sucrose particles associated with the iron (III)-hydroxide. In iron sucrose, sucrose plays the role of ligands in the core of iron hydroxide.

Therefore, in an exemplary embodiment, the iron sucrose includes one or more iron sucrose particles, and the iron sucrose particle has an iron particle in its core and one or more sucrose particles exterior to the iron particle in its core. Because the iron is located substantially at the core of its respective iron sucrose particle, the iron particle can also be referred to as the iron core particle. Fe(III) or iron (III)-hydroxide can be the iron in the iron core particle. Also, the iron core particle generally has a particle diameter in a range of about 2 nm to about 5 nm, and therefore, the iron core particle can also be referred to as an iron core nanoparticle.

Similarly, the iron sucrose particle can also be referred to as an iron sucrose nanoparticle because it generally has a particle diameter in a range of about 8 nm to about 10 nm. Likewise, in iron sucrose, the sucrose particle is generally in the nanometer range, and thus, the sucrose particle can also be referred to as a sucrose nanoparticle.

In iron sucrose, the sucrose nanoparticle acts as a ligand to the iron core nanoparticle. Thus, in some embodiments, a plurality of sucrose nanoparticles surrounds the iron core nanoparticle. In some embodiments, a plurality of sucrose nanoparticles surrounds the iron core nanoparticle by forming a shell of sucrose nanoparticles around the iron core nanoparticle. In some embodiments, the plurality of sucrose particles can be as many as 50 sucrose nanoparticles surrounding the iron core nanoparticle.

In another exemplary embodiment, the iron sucrose drug product has an iron core nanoparticle, such as Fe(III) or iron (III) hydroxide, present at a concentration, or an equivalent concentration, of about 20 mg/mL. In some embodiments, in the iron sucrose drug product, the iron core nanoparticle is present at a concentration, or an equivalent concentration, of about 20 mg/mL including but is not limited to, about 50 mg/2.5 mL, about 100 mg/5 mL, about 200 mg/10 mL, about 65 mg/3.25 mL, or about 75 mg/3.75 mL. Thus, in some embodiments, a single-use vial iron sucrose drug product contains about 2.5 mL, about 3.25 mL, about 3.75 mL, about 5 mL, or about 10 mL of the iron sucrose injectable drug product.

In some embodiments, the iron sucrose drug product includes approximately 30% sucrose w/v (weight to volume) and has a pH of approximately 10.5 to 11.1. In some embodiments, the iron sucrose drug product is a comparison product such as Venofer®, or a comparator drug product with similar characteristics (e.g., a generic version of Venofer®).

B. Other Iron Carbohydrate Drug Products

The subject matter of the present disclosure and the disclosed methods may also be applicable to other iron carbohydrate complexes, including, but not limited to, iron carbohydrate complex drug products such as high molecular weight iron dextran (e.g. Dexferrum®), low molecular weight iron dextran (e.g. Cosmofer®), sodium ferric gluconate (e.g. Ferrlecit®), iron carboxymaltose (e.g. Ferinject®, Injectafer®), and ferumoxytol (e.g. Feraheme®), or other iron carbohydrate complexes with similar characteristics.

Accordingly, in some embodiments, the iron carbohydrate complex is a high molecule weight iron dextran drug product, a low molecular weight iron dextran drug product, a sodium ferric gluconate drug product, an iron carboxymaltose drug product, or a ferumoxytol drug product.

III. Methods to Characterize Iron Core Size in Iron Carbohydrate Complexes Such as Iron Sucrose Disclosed herein are methods for characterizing the iron core particle diameter size of iron core nanoparticle in an iron carbohydrate complex, such as an iron sucrose drug product. The methods of the invention rely on small-angle X-ray scattering (SAXS). Via use of the methods disclosed herein it is possible to compare the iron core property of two samples of the same iron core particle colloid drug product by comparing their iron core particle diameter size properties as determined by SAXS. In particular, if the SAXS-determined iron core size properties (core shape, relative size distribution, average diameter, etc.) are the same or substantially same (e.g., so similar that the skilled artisan would conclude that the products are structurally similar within the margin of accuracy of SAXS), then the two samples can be assessed to have the same iron core property. The methods do not require modification of the sample, such as to remove unbound carbohydrates, dilute, or dry the sample.

In an iron sucrose drug product, the iron sucrose exhibits a colloidal system in the lower nanometer (nm) size range with an iron core nanoparticle and one or more sucrose nanoparticles surround the iron core nanoparticle. A plurality of sucrose nanoparticles can form a shell around the iron core nanoparticle, which can be referred to as a sucrose shell.

In other carbohydrate complexes, including but not limited to iron dextran, sodium ferric gluconate, iron carboxymaltose, and ferumoxytol, colloidal systems with an iron core particle and one or more carbohydrates surrounding the iron core nanoparticles is also observed. Like for iron sucrose, a plurality of carbohydrate nanoparticles can form a shell around the iron core nanoparticle.

Disclosed herein are methods to characterize the particle diameter size of the iron core nanoparticle in an iron carbohydrate complex, such as the iron core nanoparticle in iron sucrose. In iron sucrose, the iron core nanoparticle generally has a particle diameter in a range of about 2 nm to about 5 nm, and the iron sucrose particle generally has a particle diameter in a range of about 8 nm to about 10 nm. The sucrose serves as a ligand to the iron core nanoparticle, and there can be about 50 sucrose nanoparticles surrounding a single iron core nanoparticle. A ligand is an ion or particle that donates a pair of electrons to a metal atom or ion in forming a coordination complex. Therefore, because of the sucrose shell surrounding the iron core nanoparticle, characterizing the iron core nanoparticle is a technical challenge. A similar technical challenge is observed when characterizing other iron carbohydrate complexes including but not limited to iron dextran, sodium ferric gluconate, iron carboxymaltose, and ferumoxytol.

To solve this technical challenge, small-angle X-ray scattering (SAXS) was used to characterize the iron core nanoparticle in iron sucrose. SAXS is an X-ray diffraction method that measures the diffuse X-ray scattering at small scattering angles of nano-sized particles, generally in the 1-100 nm range, whose electron density of the core is significantly different from that of the carbohydrates that are tightly bound to the electron-dense core, or is unbound in the scattering medium. Generally, X-ray scattering is considered SAXS when the scattering angle (2-theta) is less than about 10 degrees, such as about 9 degrees, about 8 degrees, about 7 degrees, about 6 degrees, about 5 degrees, about 4 degrees, about 3 degrees, about 2 degrees, about 1 degree, or less. In addition, SAXS can be performed over a range of scattering angles, such as from about 0.10 degrees to about 10 degrees (or any range subsumed therein). Similar parameters can be used when using SAXS on other iron carbohydrate complexes such as iron dextran, sodium ferric gluconate, iron carboxymaltose, and ferumoxytol.

The observed SAXS scattering intensity is proportional to a structure factor component, $(1+\int (n(r)-n_o)e^{iq \cdot r} dr)$, where $n(r)$ is the particle count density function and $n_o$ is the average particle density. This structure factor component is proportional to the difference in electron density between the core particles and carbohydrates in the hydration shell of the particle and in the background medium.

Also, the observed scattering intensity is proportional to a form factor component, $N|\int(\Delta\rho(r)e^{iq \cdot r} dr|^2$, where N is the number of particles. This factor depends on the size and shape of the particles and can be fitted using various shape models (e.g. spheres, cylinder, spheroids, and core-shell). The resultant particle size distribution of the particle size can be used to determine the average core size particle diameter, $D_{10}$, $D_{50}$, $D_{90}$, and SPAN (e.g. $(D_{90}-D_{10})/D_{50}$) values for the iron core nanoparticles. The distribution can be a gamma distribution or a lognormal distribution.

Accordingly, in an exemplary embodiment, the method for characterizing average core size particle diameter size of iron core nanoparticle in iron sucrose comprises the steps of: (1) configuring an X-ray diffractometer, such as a powder X-ray diffractometer, in a parallel beam transmission geometry, and a capillary mount for the sample, for small-angle X-ray scattering (SAXS); (2) performing SAXS on an un-manipulated first sample having a plurality of iron sucrose nanoparticles to generate a first SAXS data, wherein the SAXS data includes intensity counts as a function of scattering angle, wherein each iron sucrose particle exhibits a colloidal system comprising an iron core nanoparticle and a plurality of sucrose nanoparticles surrounding the iron core nanoparticle, and wherein the SAXS is performed over a pre-determined range of scattering angles; (3) performing SAXS on a second sample comprising the same or approximately the same composition of sucrose as the first sample but no iron to generate a second SAXS data, and wherein the SAXS is performed over the pre-determined range of scattering angles with identical instrument configuration as the first sample; (4) generating a background-subtracted SAXS data by subtracting the second SAXS data from the first SAXS data, wherein the background-subtracted SAXS data includes background-subtracted intensity counts as a function of scattering angle; (5) generating a modeled background-subtracted SAXS data by modeling the background-subtracted SAXS data as a gamma distribution of different particle sizes using a projected shape of the iron core nanoparticle and a projected particle diameter size of the iron core nanoparticle, such distribution have a characteristic average diameter size and relative size distribution; and (6) calculating from the size distribution the particle size parameters of the iron core nanoparticles in the plurality of iron sucrose particles, such as average particle diameter and other $D_x$ diameters, where $D_x$ is the average diameter value where x percent of the particles are smaller than or equal to that value. Examples of $D_x$ diameters are $D_{10}$, $D_{50}$ and $D_{90}$, the diameter values at which 10, 50 and 90% of the particles are smaller than those values, respectively. The step of configuring an X-ray diffractometer, such as a powder X-ray diffractometer, in a parallel beam transmission geometry, and a capillary mount for the sample, for small-angle X-ray scattering (SAXS) may be omitted in certain embodiments.

In another exemplary embodiment, the disclosure provides methods for characterizing average iron core particle diameter size of iron core nanoparticle in an iron carbohydrate drug product (e.g., high molecular weight iron dextran (e.g., Dexferrum®), low molecular weight iron dextran (e.g., Cosmofer®), sodium ferric gluconate (e.g., Ferrlecit®), iron carboxymaltose (e.g., Ferinject®, Injectafer®), and ferumoxytol (e.g., Feraheme®)). The method steps are exactly as described for the iron sucrose embodiment. The only difference would be that the background sample is not 30% w/v sucrose but comprises the same carbohydrate of the comparator iron core carbohydrate drug product. If the identity of the carbohydrate is not exactly known, or it cannot be obtained commercially, then an approximate composition is sufficient. For example, if the carbohydrate in the drug product is 4% w/v of dextran, wherein the dextran is a pentamer of α1-6 linked glycosides, then the background sample can be 20% w/v glucose if the dextran pentamer is not available. Another potential difference is the X-ray exposure time, which depends on the iron core particle density, and one skilled in the art of SAXS would be able to easily adjust the exposure time. For example, if the SAXS intensity is less than desired, one can simply increase the exposure time.

An application of the invention, as described in the iron sucrose embodiment, is to collect separate SAXS data under identical instrument settings on two or more samples of the same iron core carbohydrate colloid drug product for the purposes of comparing their iron core particle diameter size properties. For example, if one wants to determine if two different manufacturing processes produce the same iron carbohydrate colloid drug product, one of the comparison tests one could run would be to perform identical SAXS measurements on the two samples. This application is exemplified for iron sucrose in this disclosure.

The average particle diameter size of the iron core nanoparticles can be determined based on volume-averaged or number-averaged. The terms volume-averaged (or volume-averaging) and number-averaged (or number-averaging) are generally known to one skilled in the art. To briefly illustrate the difference between these two concepts, consider a sample having three different particle sizes, such as 1 nm, 10 nm, and 100 nm. Assume that for each of these 3 sizes, there is an equal number of particles—33 particles of 1 nm, 33 particles of 10 nm, and 33 particles of 100 nm. As such, if the particle diameter size is number-averaged, then there is an equal 33% of each particle size, which also equates to a number-average of 10 nm.

By contrast, if the particle diameter size is volume-averaged, then about 90% of the total volume comes from the 100 nm particles, about 9% of the total volume comes from the 10 nm particles, and about 0.9% comes from the 1 nm particles. Thus, the particle diameter size has a volume-average of about 37 nm.

Thus, in some embodiments, the determined first and second average particle diameter sizes of the iron core nanoparticles are based on volume-averaged particle diameter sizes, and the gamma distribution data is based on a volume-averaging of the particle diameter sizes of the iron core nanoparticles. The projected particle diameter size of the iron core nanoparticle is about 4 nm to about 6 nm volume-averaged, such as about 4 nm, about 5 nm, or about 6 nm volume-averaged.

In other embodiments, the determined first and second average particle diameter sizes of the iron care nanoparticles are based on numbered-averaged particle diameter sizes, and the gamma distribution data is based on a number-averaging of the particle diameter sizes of the iron core nanoparticles. The projected particle diameter sizes of the iron core nanoparticles are about 1 nm to about 3 nm numbered-averaged, such as about 1 nm, about 2 nm, or about 3 nm number-averaged.

In some embodiments, the projected shape of the iron core nanoparticle is a sphere, a spheroid, or a cylinder, or a Debye particle of undefined shape. A spheroid is an ellipsoid with an aspect ratio which is the ratio of the longest and shortest diameter of the sphere, which is 1.0 when the spheroid is a sphere. In a preferred embodiment, the projected shape of the iron core nanoparticle is a sphere. A Debye particle is simply a particle of defined size but undefined shape.

In some embodiments, the pre-determined range of scattering angles is a range, in 2-theta (2Θ), from about 0.1 degrees to about 8 degrees, or any range subsumed therein, such as from about 0.1 degrees to about 5 degrees, from about 0.2 degrees to about 8 degrees, or from about 0.2 degrees to about 5 degrees.

In certain embodiments, the minimum effective starting 2-theta angle may be about 0.2°, alternative about 0.25°, alternatively about 0.5°, alternatively about 0.75° is required.

In some embodiments, the SAXS uses X-rays with wavelength (λ) of about 0.14 nm to about 0.16 nm, such as about 0.14 nm, about 0.15 nm, or about 0.15 nm. For example, this X-rays can be produced from a copper-based X-ray tube or can be synchrotron X-rays. However, one skilled in the art can use X-rays produced from other X-ray tubes, such as Cobalt, which has a wavelength of about 0.19 nm. In some embodiments, the intensity counts are the log of the intensity counts, and the background-subtracted intensity counts is the log of the background-subtracted intensity counts.

In iron sucrose, the sucrose nanoparticle acts as a ligand to the iron core nanoparticle. Thus, in some embodiments, a plurality of nanoparticles surrounds the iron core nanoparticle. In some embodiments, a plurality of sucrose nanoparticles surrounds the iron core nanoparticle by forming a shell of sucrose nanoparticles around the iron core nanoparticle. In some embodiments, the plurality of sucrose particles can be as many as 50 sucrose nanoparticles surrounding the iron core nanoparticle.

In some embodiments, the modeling can be performed with two or more populations of particle diameter sizes, and the average particle diameters and percent distribution size of each population are calculated.

In other embodiments, the SAXS scattering intensity is dominated by scattering from the heavier element iron, and the SAXS scattering intensity from the background sample comprising of sucrose is not significant, the modeling of the iron core nanoparticle can be performed directly from the SAXS data of the first sample alone (i.e., without using background-subtracted data).

IV. Equivalence Evaluation Criteria (EEC)

As an application of the SAXS method disclosed herein, where the SAXS-determined iron core particle diameters are compared, an equivalence evaluation criteria (EEC) can be determined using one or more of the following EEC Equations:

$$\text{EEC Lower Limit} = R_{min} * (1-\eta) \text{(herein referred to as "EEC Equation1")} \quad (1)$$

$$\text{EEC Upper Limit} = R_{max} * (1+\eta) \text{(herein referred to as "EEC Equation2")} \quad (2)$$

where $R_{min}$ and $R_{max}$ are the minimum and maximum results from the comparison set of iron sucrose samples (e.g. lots) for a tested characterization parameter, and $\eta$ is the allowable percentage tolerance range, which can be determined based on the comparison set's "Extreme Range" (E-range or $E_{range}$) that is defined as follows:

$$E_{Range} = \frac{R_{Max} - R_{Min}}{R_{Mean}} \times 100\% \quad (3)$$

(herein referred to as "EEC Equation 3")

$\eta$ is reasonably assigned as higher of 10% and a half of $E_{Range}$, namely $$\eta = \text{Max}\left(10\%, \frac{1}{2}E_{Range}\right) \quad (4)$$

(herein referred to as "EEC Equation 4")

If $E_{Range}$ is used, $\eta$ will be round-off to the higher 5%, thus the value of $\eta$ could be 10%, 15%, or 20% ... depending on the experimental results of $E_{Range}$ for the tested characterization parameters.

In certain embodiments, if the particle diameters of the test set are within the EEC max and min values of the comparison set, then their iron core nanoparticles can be judged to be the same.

In other embodiments, the methods further include determining a first set of one or more $D_x$ values based on the first gamma distribution; and determining a second set of one or more $D_x$ based on the second gamma distribution; wherein the $D_x$ is a particle diameter size of the iron core nanoparticles in the respective sample in which x % of the iron core nanoparticles are smaller than the average particle diameter size of the iron core nanoparticles in the respective sample.

In still other embodiments, the methods further include the one or more $D_x$ having a $D_{10}$, a $D_{50}$, and a $D_{90}$. The $D_{10}$ is a particle diameter size of the iron core nanoparticle in the respective sample in which 10% of the iron core nanoparticles are smaller than the average value of the particle diameter size of the iron core nanoparticles in the respective sample; the $D_{50}$ is a particle diameter size of the iron core nanoparticles in the respective sample in which 50% of the iron core nanoparticles are smaller than the average value of the particle diameter size of the iron core nanoparticles in the respective sample; and the $D_{90}$ is a particle diameter size of the iron core nanoparticles in the respective sample in which 90% of the iron core nanoparticles are smaller than the average value of the particle diameter size of the iron core nanoparticles in the respective sample. In other embodiments, $D_x$ can be $D_5$, $D_{15}$, $D_{20}$, $D_{25}$, $D_{30}$, $D_{35}$, $D_{40}$, $D_{45}$, $D_{55}$, $D_{60}$, $D_{65}$, $D_{70}$, $D_{75}$, $D_{80}$, $D_{85}$, or $D_{95}$.

In some embodiments, the methods further include determining a first SPAN based on the first set of $D_x$; and determining a second SPAN based on the second set of $D_x$; wherein the SPAN is determined based on:

$$\text{SPAN} = (D_{90} - D_{10})/D_{50}.$$

In some embodiments, the EEC has a percent tolerance of 10%. In other embodiments, the EEC has a percent tolerance of 5%, 15%, 20%, 25%, or any other suitable differential. In some embodiments, EEC of the $D_{50}$ and SPAN parameters are compared while in other embodiments, one or more of these EEC equations are compared.

V. Combination with Other Methods

In certain embodiments of the invention, the methods of the invention may be used in combination with other methods suitable for characterizing samples of the same iron carbohydrate drugs in such a way as to demonstrate that they are structurally similar. For example, the methods of the invention may be used in combination with the methods characterizing iron core size in iron carbohydrate complexes, such as e.g. iron sucrose, including iron sucrose drug products via nuclear magnetic resonance (NMR) disclosed in U.S. Provisional Application No. 63/019,867 (filed on May 4, 2020) and PCT Application No. PCT/US2021/030670 (filed May 4, 2021), the disclosures of which are herein incorporated in their entirety as they pertain to methods of characterizing iron carbohydrates via NMR.

VI. Additional Embodiments

Other embodiments of the invention are directed to systems configured to perform the methods of the disclosure. For example, one embodiment of the invention is a point-collimation instrument configured to perform the SAXS methods of the disclosure. Another embodiment of the invention is a line-collimation instrument configured to perform the SAXS methods of the disclosure.

In yet additional embodiments of the invention include generation of the putative iron carbohydrate drug before testing the compound using the methods of the invention.

Additional embodiments of the invention include a computer program product (embodied on a non-transitory computer readable medium and having code adapted to be executed by a computer to perform the methods of the invention).

Yet another embodiment of the invention is directed to a method of treating iron deficiency anemia comprising identifying an iron carbohydrate product for treating iron deficiency anemia that has the same iron core size property as determined using the methods described herein as a commercially available one, and administering the iron carbohydrate product to a patient suffering from anemia.

VII. Illustrative Embodiments

Provided here are illustrative embodiments of the disclosed technology. These embodiments are illustrative only and do not limit the scope of the present disclosure or of the claims attached.

A. Illustrative Embodiments of Assessing Iron Sucrose Particle Size

Embodiment 1. A method for characterizing an average iron core particle diameter size of iron core nanoparticles in iron sucrose comprising the steps of: (1) configuring an X-ray diffractometer, such as a powder X-ray diffractometer, in a parallel beam transmission geometry, and optionally a capillary mount for the sample, for small-angle X-ray scattering (SAXS); (2) performing SAXS on a first sample having a plurality of iron sucrose particles to generate a first SAXS data, herein labelled the Test data, wherein the SAXS data includes intensity counts as a function of scattering angle, wherein each iron sucrose particle exhibits a colloidal system comprising an iron core nanoparticle and a plurality of sucrose nanoparticles surrounding the iron core nanoparticle, and wherein the SAXS is performed over a pre-determined range of scattering angles; (3) performing SAXS on a second sample comprising the same composition of sucrose as the first sample but no iron to generate a second SAXS data, herein labelled the Blank data, and wherein the SAXS is performed over the pre-determined range of scattering angles with identical instrument settings as the first sample; (4) generating a background-subtracted SAXS data by subtracting the Blank data from the Test data, wherein the background-subtracted SAXS data includes background-subtracted intensity counts as a function of scattering angle; (5) generating a modeled background-subtracted SAXS data by modeling the background-subtracted SAXS data as a gamma distribution of different particle sizes using a projected shape of the iron core nanoparticle and a projected particle diameter size of the iron core nanoparticle, such distribution have a characteristic average particle diameter size and relative size distribution; and (6) calculating from the size distribution the particle size parameters of the iron core nanoparticles in the plurality of iron sucrose particles, such as average particle diameter and other $D_x$ diameters, where $D_x$ is the average diameter value where x percent of the particles are smaller than or equal to that value. Examples of $D_x$ diameters are $D_{10}$, $D_{50}$ and $D_{90}$, the diameter values at which 10, 50 and 90% of the particles are smaller than those values, respectively. The step of configuring an X-ray diffractometer, such as a powder X-ray diffractometer, in a parallel beam transmission geometry, and a capillary mount for the sample, for small-angle X-ray scattering (SAXS) may be omitted or may be optional.

Embodiment 2. The method of embodiment 1, wherein a separate SAXS data is collected under identical instrument settings on two or more samples of the same iron core carbohydrate colloid drug product for the purposes of comparing their iron core particle diameter size properties. For example, if one wants to determine if two different manufacturing processes produce the same iron core carbohydrate colloid drug product, one of the comparison tests one could run would be to perform identical SAXS measurements on the two samples. This application is exemplified for iron sucrose in the previous disclosures.

Embodiment 3. The method of any one of embodiments 1-2, wherein the determined average particle diameter sizes of the iron core nanoparticles are based on volume-averaged particle diameter sizes, and wherein the gamma distribution data is based on a volume-averaging of the particle diameter sizes of the iron core nanoparticles.

Embodiment 4. The method of embodiment 3, wherein the projected particle diameter size of the iron core nanoparticle is about 4 nm to about 6 nm volume-averaged.

Embodiment 5. The method of embodiment 4, wherein the projected particle diameter size of the iron core nanoparticle is about 5 nm volume-averaged.

Embodiment 6. The method of any one of embodiments 1-2, wherein the determined average particle diameter sizes of the iron core nanoparticles are based on numbered-averaged particle diameter sizes, and wherein the gamma distribution data is based on a number-averaging of the particle diameter sizes of the iron core nanoparticles.

Embodiment 7. The method of embodiment 6, wherein the projected particle diameter sizes of the iron core nanoparticle is about 1 nm to about 3 nm numbered-averaged.

Embodiment 8. The method of embodiment 7, wherein the projected particle diameter sizes of the iron core nanoparticle is about 2 nm numbered-averaged.

Embodiment 9. The method of any one of embodiments 1-2, wherein the projected shape of the iron core nanoparticle is select from the group consisting of a sphere, a spheroid, a cylinder, or a Debye particle of undefined shape. A core shell shape may also be selected if there is other evidence that the core has this type of shape.

Embodiment 10. The method of any one of embodiments 1-2, wherein the projected shape of the iron core nanoparticle is a sphere.

Embodiment 11. The method of any one of embodiments 1-2, wherein the pre-determined range of scattering angles is a range, in 2-theta (2Θ), from about 0.1 degrees to about 8 degrees.

Embodiment 12. The method of any one of embodiments 1-2, wherein the pre-determined range of scattering angles is a range, in 2-theta (2Θ), from about 0.1 degrees to about 5 degrees.

Embodiment 13. The method of any one of embodiments 1-2, wherein the pre-determined range of scattering angles is a range, in 2-theta (2Θ), from about 0.2 degrees to about 8 degrees.

Embodiment 14. The method of any one of embodiments 1-2, wherein the pre-determined range of scattering angles is a range, in 2-theta (2Θ), from about 0.2 degrees to about 5 degrees.

Embodiment 15. The method of any one of embodiments 1-14, further comprising the steps of: determining a set of equivalence evaluation criteria (EEC), wherein the set of EEC comprises at least one EEC based on the average particle diameter size of a set of comparison samples of iron core nanoparticles; and each EEC is based on a range of [minimum value multiplied by (1 minus percent tolerance)] and [maximum value multiplied by (1 plus percent tolerance)]; and determining whether the average particle diameter size of the iron core nanoparticles of the Test sample meets the EEC.

Embodiment 16. The method of embodiment 15, wherein the percent tolerance is 10%.

Embodiment 17. The method of any one of embodiments 1-14, further comprising the steps of: determining one or more $D_x$ based on the gamma distribution data of the Test set; and determining one or more $D_x$ based on the gamma distribution data of the comparison sample; wherein the $D_x$ is a particle diameter size of the iron core nanoparticles in the respective sample in which x % of the iron core nanoparticles have a particle diameter size less than the $D_x$.

Embodiment 18. The method of embodiment 17, wherein the one or more $D_x$ includes a $D_{10}$, a $D_{50}$, and a $D_{90}$, wherein: the $D_{10}$ is a particle diameter size of the iron core nanoparticles in the respective sample in which 10% of the iron core nanoparticles have a particle diameter size less than the $D_{10}$; the $D_{50}$ is a particle diameter size of the iron core nanoparticles in the respective sample in which 50% of the iron core nanoparticles have a particle diameter size less than the $D_{50}$ and 50% of the iron core nanoparticles have a particle diameter size more than the $D_{80}$; and the $D_{90}$ is a particle diameter size of the iron core nanoparticles in the respective sample in which 90% of the iron core nanoparticles have a particle diameter size less than the $D_{90}$.

Embodiment 19. The method of embodiment 18, further comprising the step of: determining a SPAN based on the Test set of $D_x$; and determining a SPAN based on the $D_x$ values of the comparison sample; wherein the SPAN is determined based on $(D_{90}-D_{10})/D_{50}$.

Embodiment 20. The method of embodiment 17, further comprising the steps of: determining a set of equivalence evaluation criteria (EEC), wherein the set of EEC comprises at least four EECs based on the average particle diameter size and $D_x$ values of the set of comparison samples of iron core nanoparticles, and each EEC is based on a range of [minimum value multiplied by (1 minus percent tolerance)] and [maximum value multiplied by (1 plus percent tolerance)]; and determining whether the average particle diameter size and $D_x$ values of the Test sample of the iron core nanoparticles meets the corresponding EEC of the comparison set.

Embodiment 21. The method of embodiment 20, wherein the tolerance is ±10%.

Embodiment 22. The method of embodiment 20, wherein the $D_x$ includes the $D_{10}$, the $D_{50}$, and the $D_{90}$.

Embodiment 23. The method of embodiment 20, wherein the set of EEC further includes the SPAN, wherein the SPAN is determined based on $(D_{90}-D_{10})/D_{50}$.

Embodiment 24. The method of any one of embodiments 1-14, further comprising the steps of: determining a set of equivalence evaluation criteria (EEC), wherein the set of EEC comprises at least one EEC based on the average particle diameter size of the set of comparison samples of the iron core nanoparticles; and each EEC is determined based on EEC Equations 1, 2, 3, and 4, with $\eta=10\%$; and determining whether the average particle diameter of the Test sample of the iron core nanoparticles size meets the EEC of the comparison set.

Embodiment 25. The method of any one of embodiments 1-24, wherein the plurality of sucrose nanoparticles serves as a ligand to the iron core nanoparticle.

Embodiment 26. The method of any one of embodiments 1-24, wherein the plurality of sucrose nanoparticles surrounds the iron core nanoparticle by forming a shell of sucrose nanoparticles around the iron core nanoparticle.

Embodiment 27. The method of any one of embodiments 1-24, wherein the plurality of sucrose particle is up to about 50 sucrose particles.

Embodiment 28. The method of any one of embodiments 1-24, wherein the modeling is performed using a modeling software.

Embodiment 29. The method of any one of embodiments 1-24, wherein the SAXS uses a wavelength of about 0.14 nm to about 0.16 nm.

Embodiment 30. The method of any one of embodiments 1-24, wherein the SAXS uses a wavelength of about 0.15 nm.

Embodiment 31. The method of any one of embodiments 2-24, wherein the Test product iron sucrose drug product and the comparison product both have an equivalent concentration of about 20 mg/mL of iron.

Embodiment 32. The method of any one of embodiments 1-24, wherein the intensity counts is the log of the intensity counts, and the background-subtracted intensity counts is the log of the background-subtracted intensity counts.

Embodiment 33. The method of any one of embodiments 1-24, wherein modelling is performed on the raw, non-background subtracted, X-ray intensities. For example, when the diffraction from the Blank sample is insignificant compared with the iron core nanoparticle colloid drug product, or when the identity of the carbohydrate component is unknowable.

Embodiment 34. A point-collimation instrument or line-collimation instrument configured to perform the methods of any one of embodiments 1-33.

Embodiment 35. A computer program product on a non-transitory computer readable medium and having code adapted to be executed by a computer to perform the methods of any one of embodiments 1-33.

B. Further Illustrative Embodiments

Embodiment 1. A method for characterizing an average iron core particle diameter size of iron core nanoparticles in an iron carbohydrate drug product comprising the steps of: (1) configuring an X-ray diffractometer, such as a powder X-ray diffractometer, in a parallel beam transmission geometry, and optionally a capillary mount for the sample, for small-angle X-ray scattering (SAXS); (2) performing SAXS on a first sample having a plurality of iron carbohydrate particles to generate a first SAXS data, herein labelled the Test data, wherein the SAXS data includes intensity counts as a function of scattering angle, wherein each iron carbohydrate particle exhibits a colloidal system comprising an iron core nanoparticle and a plurality of carbohydrate nanoparticles surrounding the iron core nanoparticle, and wherein the SAXS is performed over a pre-determined range of scattering angles; (3) performing SAXS on a second sample comprising the same composition of sucrose as the first sample but no iron to generate a second SAXS data, herein labelled the Blank data, and wherein the SAXS is performed over the pre-determined range of scattering angles with identical instrument settings as the first sample; (4) generating a background-subtracted SAXS data by subtracting the second Blank data from the Test data, wherein the background-subtracted SAXS data includes background-subtracted intensity counts as a function of scattering angle; (5) generating a modeled background-subtracted SAXS data by modeling the background-subtracted SAXS data as a gamma distribution of different particle sizes using a projected shape of the iron core nanoparticle and a projected particle diameter size of the iron core nanoparticle, such distribution have a characteristic average particle diameter size and relative size distribution; and (6) calculating from the size distribution the particle size parameters of the iron core nanoparticles in the plurality of iron sucrose particles, such as average particle diameter and other $D_x$ diameters, where $D_x$ is the average diameter value where x percent of the particles are smaller than or equal to that value. Examples of $D_x$ diameters are $D_{10}$, $D_{50}$ and $D_{90}$, the diameter values at which 10, 50 and 90% of the particles are smaller than those values, respectively. The step of configuring an X-ray diffractometer, such as a powder X-ray diffractometer, in a parallel beam transmission geometry, and a capillary mount for the sample, for small-angle X-ray scattering (SAXS) may be omitted or may be optional.

Embodiment 2. The method of embodiment 1, wherein a separate SAXS data is collected under identical instrument settings on two or more samples of the same iron core carbohydrate colloid drug product for the purposes of comparing their iron core particle diameter size properties. For example, if one wants to determine if two different manufacturing processes produce the same iron core carbohydrate colloid drug product, one of the comparison tests one could run would be to perform identical SAXS measurements on the two samples. This application is exemplified for iron sucrose in the previous disclosures.

Embodiment 3. The method of embodiments 1 or 2, wherein the iron carbohydrate drug product is iron sucrose, a high molecule weight iron dextran drug product, a low molecular weight iron dextran drug product, a sodium ferric gluconate drug product, an iron carboxymaltose drug product, or a ferumoxytol drug product.

Embodiment 4. A method for characterizing an average iron core particle diameter size of iron core nanoparticles in iron sucrose comprising the steps of: (1) performing SAXS on a first sample having a plurality of iron sucrose particles to generate a first SAXS data, herein labelled the Test data, wherein the SAXS data includes intensity counts as a function of scattering angle, wherein each iron sucrose particle exhibits a colloidal system comprising an iron core nanoparticle and a plurality of sucrose nanoparticles surrounding the iron core nanoparticle, and wherein the SAXS is performed over a pre-determined range of scattering angles; (2) performing SAXS on a second sample comprising the same composition of sucrose as the first sample but no iron to generate a second SAXS data, herein labelled the Blank data, and wherein the SAXS is performed over the pre-determined range of scattering angles with identical instrument settings as the first sample; (3) generating a background-subtracted SAXS data by subtracting the second Blank data from the Test data, wherein the background-subtracted SAXS data includes background-subtracted intensity counts as a function of scattering angle; (4) generating a modeled background-subtracted SAXS data by modeling the background-subtracted SAXS data as a gamma distribution of different particle sizes using a projected shape of the iron core nanoparticle and a projected particle diameter size of the iron core nanoparticle, such distribution have a characteristic average particle diameter size and relative size distribution; and (5) calculating from the size distribution the particle size parameters of the iron core nanoparticles in the plurality of iron sucrose particles, such as average particle diameter and other $D_x$ diameters, where $D_x$ is the average diameter value where x percent of the particles are smaller than or equal to that value. Examples of $D_x$ diameters are $D_{10}$, $D_{50}$ and $D_{90}$, the diameter values at which 10, 50 and 90% of the particles are smaller than those values, respectively. The method may include the step of configuring an X-ray diffractometer, such as a powder X-ray diffractometer, in a parallel beam transmission geometry, and a capillary mount for the sample, for small-angle X-ray scattering (SAXS) prior to performing SAXS.

Embodiment 5. The method of embodiment 4, wherein a separate SAXS data is collected under identical instrument settings on two or more samples of the same iron core carbohydrate colloid drug product for the purposes of comparing their iron core particle diameter size properties. For example, if one wants to determine if two different manufacturing processes produce the same iron core carbohydrate colloid drug product, one of the comparison tests one could run would be to perform identical SAXS measurements on the two samples. This application is exemplified for iron sucrose in the previous disclosures.

Embodiment 6. The method of any one of embodiments 1-5, wherein the determined average particle diameter sizes of the iron core nanoparticles are based on volume-averaged particle diameter sizes, and wherein the gamma distribution data is based on a volume-averaging of the particle diameter sizes of the iron core nanoparticles.

Embodiment 7. The method of embodiment 6, wherein the projected particle diameter size of the iron core nanoparticle is about 4 nm to about 6 nm volume-averaged.

Embodiment 8. The method of embodiment 7, wherein the projected particle diameter size of the iron core nanoparticle is about 5 nm volume-averaged.

Embodiment 9. The method of any one of embodiments 1-5, wherein the determined average particle diameter sizes of the iron core nanoparticles are based on numbered-averaged particle diameter sizes, and wherein the gamma distribution data is based on a number-averaging of the particle diameter sizes of the iron core nanoparticles.

Embodiment 10. The method of embodiment 9, wherein the projected particle diameter sizes of the iron core nanoparticle is about 1 nm to about 3 nm numbered-averaged.

Embodiment 11. The method of embodiment 10, wherein the projected particle diameter sizes of the iron core nanoparticle is about 2 nm numbered-averaged.

Embodiment 12. The method of any one of embodiments 1-11, wherein the projected shape of the iron core nanoparticle is selected from the group consisting of a sphere, a spheroid, a cylinder, a core shell, and a Debye particle of undefined shape. A core shell shape may be selected if there is other evidence that the core has this type of shape.

Embodiment 13. The method of embodiments 12, wherein the projected shape of the iron core nanoparticle is a sphere.

Embodiment 14. The method of any one of embodiments 1-13, wherein the pre-determined range of scattering angles is: a range, in 2-theta (2Θ), from about 0.1 degrees to about 8 degrees; a range, in 2-theta (2Θ), from about 0.1 degrees to about 5 degrees; a range, in 2-theta (2Θ), from about 0.2 degrees to about 8 degrees; or a range, in 2-theta (2Θ), from about 0.2 degrees to about 5 degrees.

Embodiment 15. The method of embodiments 2 and 5, further comprising the steps of: determining a set of equivalence evaluation criteria (EEC), wherein the set of EEC comprises at least one EEC based on the average particle diameter size of the set of comparison samples of iron core nanoparticles; and each EEC is based on a range of [minimum value multiplied by (1 minus percent tolerance)] and [maximum value multiplied by (1 plus percent tolerance)]; and determining whether the average particle diameter size of the Test sample of iron core nanoparticles meets the EEC.

Embodiment 16. The method of embodiment 15, wherein the percent tolerance is 10%.

Embodiment 17. The method of any one of embodiments 2 or 5-16, further comprising the steps of: determining a first set of one or more $D_x$ based on the first gamma distribution data; and determining a second set of one or more $D_x$ based on the second gamma distribution data; wherein the $D_x$ is a particle diameter size of the iron core nanoparticles in the respective sample in which x % of the iron core nanoparticles have a particle diameter size less than the $D_x$.

Embodiment 18. The method of embodiment 17, wherein the one or more $D_x$ includes a $D_{10}$, a $D_{50}$, and a $D_{90}$, wherein: the $D_{10}$ is a particle diameter size of the iron core nanoparticles in the respective sample in which 10% of the iron core nanoparticles have a particle diameter size less than the $D_{10}$; the $D_{50}$ is a particle diameter size of the iron core nanoparticles in the respective sample in which 50% of the iron core nanoparticles have a particle diameter size less than the $D_{50}$ and 50% of the iron core nanoparticles have a particle diameter size more than the $D_{50}$; and the $D_{90}$ is a particle diameter size of the iron core nanoparticles in the respective sample in which 90% of the iron core nanoparticles have a particle diameter size less than the $D_{90}$.

Embodiment 19. The method of embodiment 18, further comprising the step of: determining a first SPAN based on the first set of $D_x$; and determining a second SPAN based on the second set of $D_x$; wherein the SPAN is determined based on $(D_{90}-D_{10})/D_{50}$.

Embodiment 20. The method of embodiment 17, further comprising the steps of: determining a set of equivalence evaluation criteria (EEC), wherein the set of EEC comprises at least four EECs based on the second average particle diameter size of the iron core nanoparticles and the second set of $D_x$, and each EEC is based on a range of [minimum value multiplied by (1 minus percent tolerance)] and [maximum value multiplied by (1 plus percent tolerance)]; and determining whether the first average particle diameter size of the iron core nanoparticles and the first set of $D_x$ meets the corresponding EEC in the set of EEC.

Embodiment 21. The method of embodiment 20, wherein the tolerance is +10%.

Embodiment 22. The method of embodiments 20 or 21, wherein the first and second set of $D_x$ includes the $D_{10}$, the $D_{50}$, and the $D_{90}$.

Embodiment 23. The method of any one of embodiments 20-23, wherein the set of EEC further includes the SPAN, wherein the SPAN is determined based on $(D_{90}-D_{10})/D_{50}$.

Embodiment 24. The method of embodiments 2 or 5, further comprising the steps of: determining a set of equivalence evaluation criteria (EEC), wherein the set of EEC comprises at least one EEC based on the second average particle diameter size of the iron core nanoparticles; and each EEC is determined based on EEC Equations 1, 2, 3, and 4, with $\eta=10\%$; and determining whether the first average particle diameter of the iron core nanoparticles size meets the EEC.

Embodiment 25. The method of any one of embodiments 1-24, wherein the plurality of sucrose nanoparticles serves as a ligand to the iron core nanoparticle.

Embodiment 26. The method of any one of embodiments 4-25, wherein the plurality of sucrose nanoparticles surrounds the iron core nanoparticle by forming a shell of sucrose nanoparticles around the iron core nanoparticle.

Embodiment 27. The method of any one of embodiments 4-25, wherein the plurality of sucrose particle is up to about 50 sucrose particles.

Embodiment 28. The method of any one of embodiments 1-27, wherein the modeling is performed using a modeling software.

Embodiment 29. The method of any one of embodiments 1-27, wherein the SAXS uses a wavelength of about 0.14 nm to about 0.16 nm.

Embodiment 30. The method of embodiment 29, wherein the SAXS uses a wavelength of about 0.15 nm.

Embodiment 31. The method of any one of embodiments 1-5, wherein the tested drug product and the comparison product both have an equivalent concentration of about 20 mg/mL of iron.

Embodiment 32. The method of any one of embodiments 1-31, wherein the intensity counts is the log of the intensity counts, and the background-subtracted intensity counts is the log of the background-subtracted intensity counts.

Embodiment 33. The method of any one of embodiments 1-24, wherein modelling is performed on the raw, non-background subtracted, X-ray intensities. For example, when the diffraction from the Blank sample is insignificant compared with the iron core nanoparticle colloid drug product, or when the identity of the carbohydrate component is unknowable.

Embodiment 34. A point-collimation instrument or line-collimation instrument configured to perform the methods of any one of embodiments 1-33.

Embodiment 35. A computer program product on a non-transitory computer readable medium and having code adapted to be executed by a computer to perform the methods of any one of embodiments 1-33.

Without further description, it is believed that one of ordinary skill in the art can, using the preceding description and the following illustrative examples, make and utilize the present invention and practice the claimed methods. The following working examples, therefore, specifically point out the preferred embodiments of the present invention and are not to be construed as limiting in any way the remainder of the disclosure.

EXAMPLES

Example 1—Characterization of the Iron Core Nanoparticle Size in Iron Sucrose Drug Products In Example 1, SAXS in transmission diffraction geometry was applied with identical instrument settings to three different sample types mounted in a capillary on a Rigaku SmartLab SE X-ray system configured in parallel-beam transmission geometry for SAXS, having X-rays generated from a copper-based X-ray tube with a wavelength (k) of about 0.14 nm to about 0.15 nm, and a 2-theta sampling range from 0.1° to 8° using a 2-theta step size of 0.03°. The first sample type includes six (6) test lots of tested product (i.e., iron sucrose drug product) having iron present at an equivalent concentration of about 20 mg/mL, and is labelled I002. The second sample type is a water solution comprising sucrose molecules without any iron present, and specifically, 30% w/v (weight to volume) sucrose, and is labelled Blank. The third sample type includes six (6) lots of a comparison product for iron sucrose, and specifically, Venofer® having iron present at an equivalent concentration of about 20 mg/mL, and is labelled RLD. The iron sucrose drug product samples have a plurality of iron sucrose particles and each iron sucrose particle exhibits a colloidal system comprising an iron core nanoparticle and a plurality of sucrose nanoparticles surrounding the iron core nanoparticle by forming a shell of sucrose nanoparticles around the iron core nanoparticle. The plurality of sucrose nanoparticles serves as a ligand to the iron core nanoparticle.

For each of the three sample types, SAXS data were collected using identical instrument settings. The SAXS data included intensity counts (Y-axis) as a function of the 2-theta scattering angle (X-axis). The intensity counts can also be presented as the log of the intensity counts for display purposes, such as in FIG. 1 (i.e. the modelling is not affected by whether the X-ray intensity is displayed as intensity counts, or log of the intensity counts).

FIG. 1 is a graph showing the SAXS data from the performed SAXS on the two iron sucrose drug product samples and the sucrose only sample. SAXS was also performed on an empty capillary. For simplicity, the SAXS data is shown only for one lot from each of the two iron sucrose drug products. In particular, in FIG. 1, the Y-axis is the "Log intensity (counts)," which is the log of the intensity counts, and the X-axis is the "2-Theta (degree)," which is the scattering angle. Table 1 provides the legends for FIGS. 1-5.

TABLE 1

Legend for FIGS. 1-5.

| Legend | Description |
|---|---|
| Empty capillary | Diffraction of an empty capillary. |
| I002 | First sample type - Tested product iron sucrose drug product (Equivalent concentration of iron 20 mg/mL). |
| Blank | Second sample type - A water solution comprising 30% w/v sucrose. |
| RLD | Third sample type - comparator product for iron sucrose (Venofer ®, Equivalent concentration of iron 20 mg/mL). |

Next, for each lot of the tested product I002, a background-subtracted SAXS data was generated by subtracting the Blank SAXS data from the I002 SAXS data. The background-subtracted SAXS data includes background-subtracted intensity counts as a function of scattering angle. Similarly, for each lot of the comparison product samples, a background-subtracted SAXS data was generated by subtracting the Blank SAXS data from the RLD SAXS data.

In Example 1, the modeling of the iron core includes modeling the projected shape of a sphere for the iron core nanoparticles, and modeling a projected particle diameter size of the iron core nanoparticle of about 5 nm volume-averaged and about 2 nm number-averaged. The modeling can be performed using a modeling software. In Example 1, the modeling software used was NANO-Solver by Rigaku.

Figure 2:
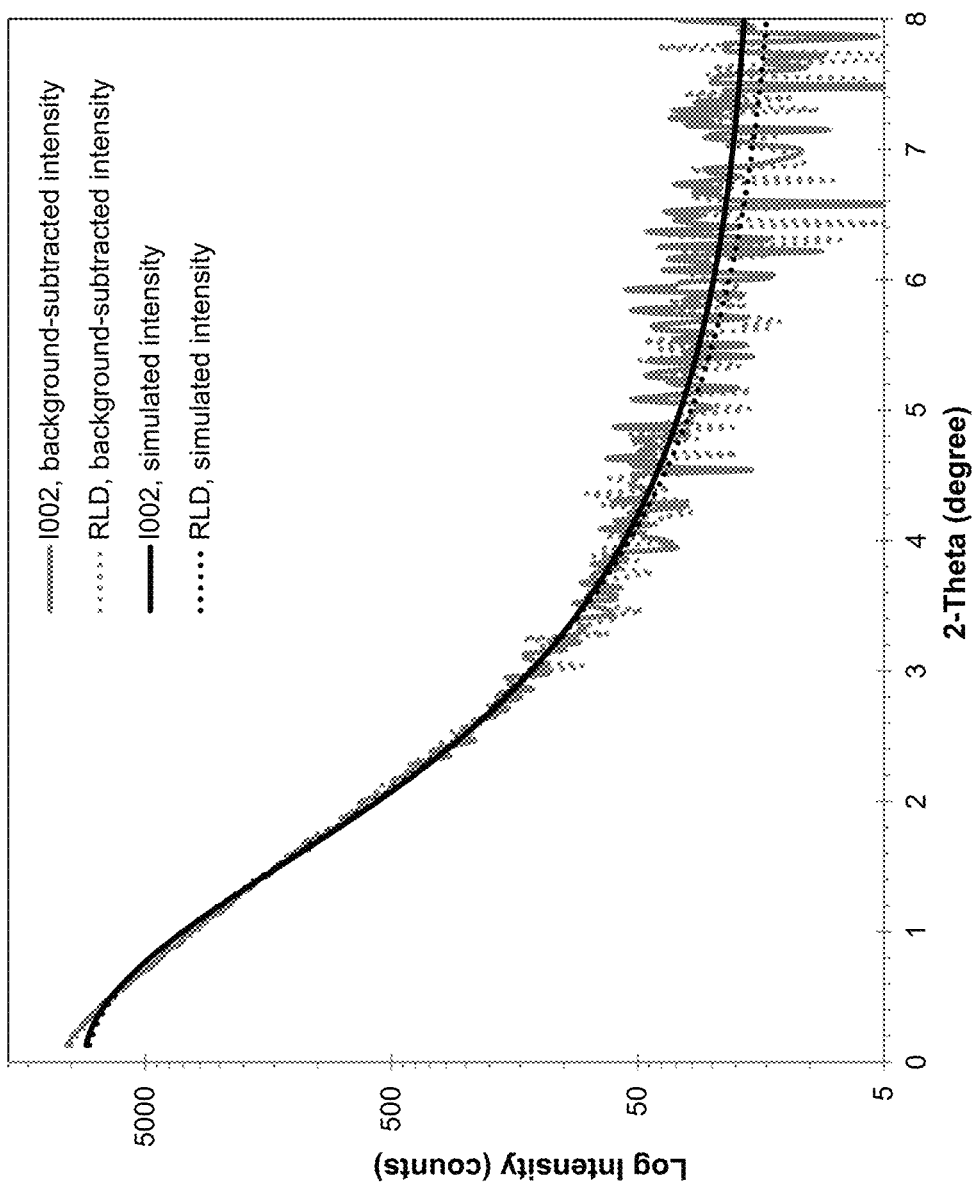
FIG. 2 is a graph showing the log intensity of the modeled and unmodeled background-subtracted scattering intensity for an iron core in iron sucrose.

FIG. 2 shows the background-subtracted scattering intensity profile (modeled and unmodeled) of Example 1, depicted on the Y-axis as "Log Intensity (counts)", as a function of the diffraction angle, 2 theta (Θ) in degrees, depicted on the X-axis as "2-Theta (degree)." More particularly, FIG. 2 shows the modeled and unmodeled background-subtracted SAXS data of the first sample type tested product I002 and of the third sample type (comparison product, RLD) in the form of background-subtracted intensity profiles. The unmodeled background-subtracted SAXS data is the observed background-subtracted SAXS data. In FIG. 2, the modeled background-subtracted SAXS data is represented by the I002 and the RLD "simulated intensity" data sets, and the unmodeled background-subtracted SAXS data is represented by the I002 and RLD "background-subtracted intensity" data sets.

Figure 3:
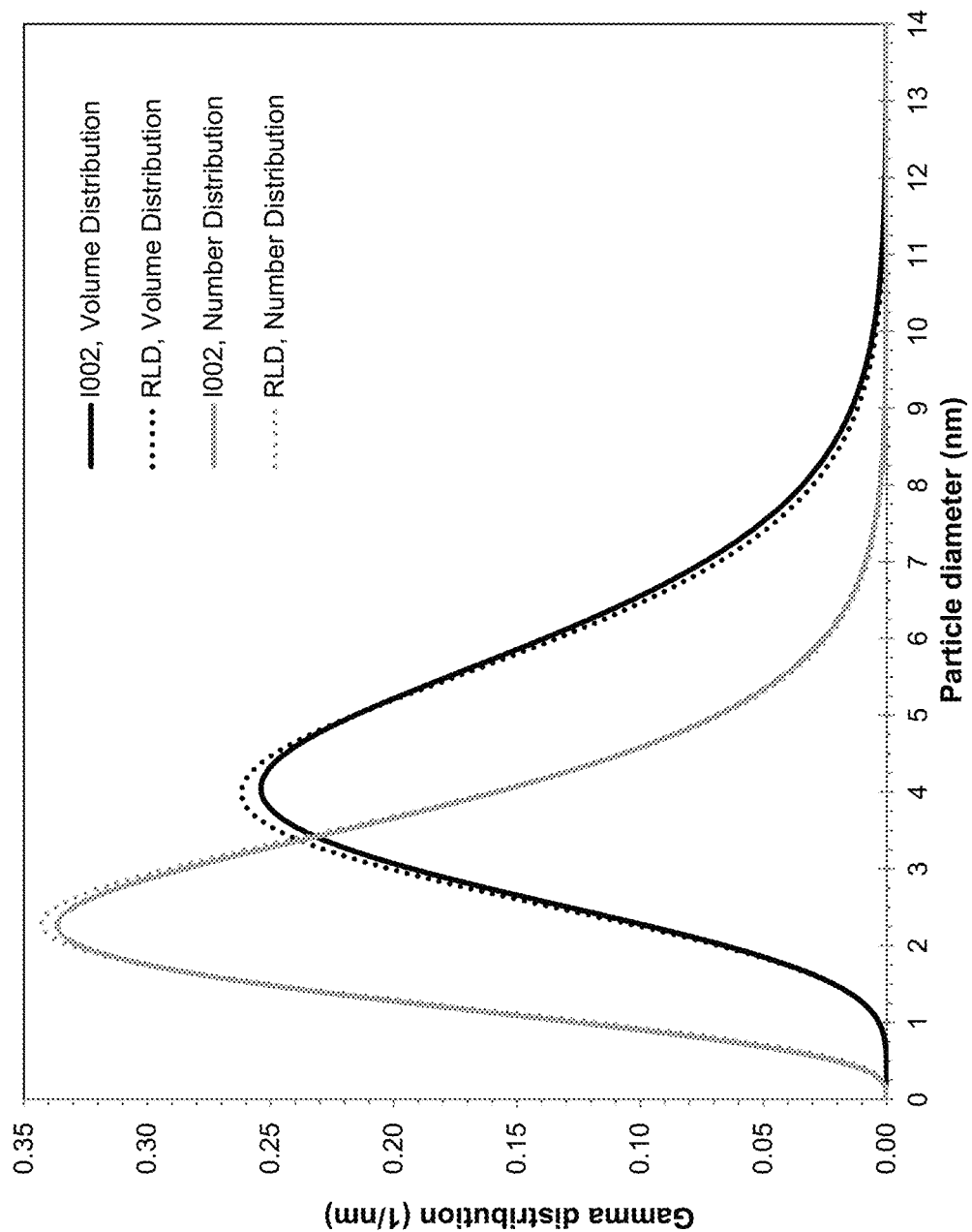
FIG. 3 is a graph illustrating the gamma distribution versus particle size diameter of an iron core in iron sucrose, shown for both volume and number-averaged calculations.

Next, for each lot of the twelve (12) lots of the iron sucrose drug product samples, gamma distribution data is generated based on the respective modeled background-subtracted SAXS data, as shown in FIG. 3. FIG. 3 illustrates the gamma distribution of the average particle diameter sizes of the iron core nanoparticles where the Y-axis is the gamma distribution (1/nm), the X-axis is the particle diameter size (nm). In FIG. 3, the gamma distribution data includes a gamma distribution as a function of particle size. As depicted in FIG. 3, the gamma distribution data was calculated using both number-averaging and volume-averaging of the particle diameter size of the iron core nanoparticles. In FIG. 3, the number-averaged particle diameter size data sets are represented by the I002 and the RLD "Number Distribution" data sets, and the volume-averaged particle diameter size data sets are represented by the I002 and the RLD "Volume Distribution" data sets.

Figure 4:
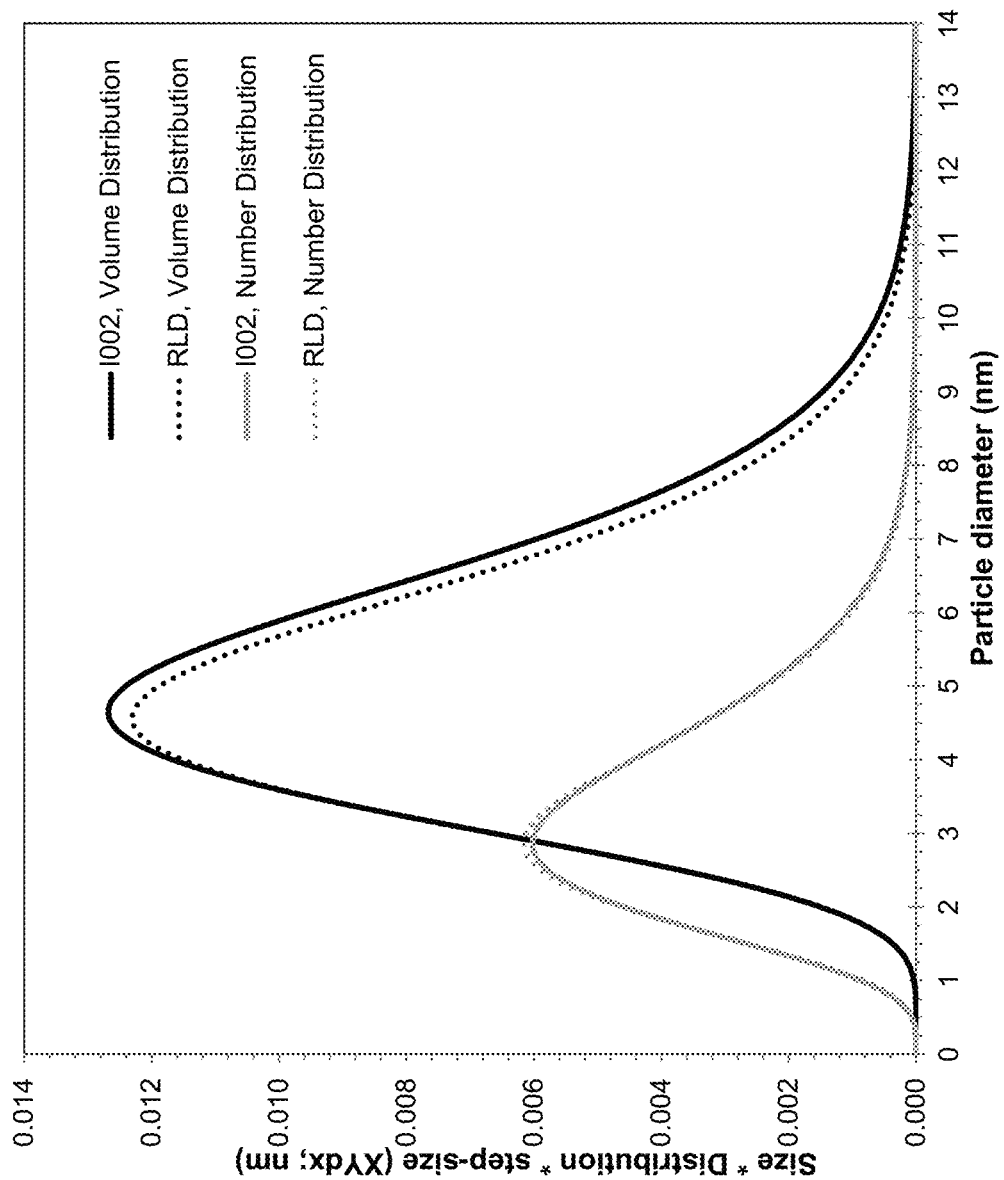
FIG. 4 is a graph illustrating the average particle size diameter of an iron core in iron sucrose. The sum of the area under the curve is the average particle size.

For each lot of the twelve (12) lots of the iron sucrose drug product samples, the average particle diameter size and relative size distribution of the iron core nanoparticles are outputted by the modeling software, along with the gamma distribution data. From these two values, the standard deviation of the particle diameter size can be calculated as the product of the average particle size and relative size distribution. One could also calculate the average particle diameter size from the gamma distribution data itself. In particular, FIG. 4 depicts the "XYdx" plot where the Y-axis represent "XYdx" in nm and the X-axis represents the particle diameter size (nm) of the iron core nanoparticles. In the Y-axis of "XYdx", "X" is the particle diameter size of the iron core nanoparticles in nm, "Y" is the gamma distribution in 1/nm, and "dx" is the step size in the particle diameter size. In FIG. 4, the "dx" is based on the entire particle size diameter range of 0 nm to about 20 nm. The average particle diameter of the iron core of the iron core nanoparticles is the sum of the XYdx values over the entire range of particle sizes, and these results are detailed in Tables 2 and 3. To highlight the details of the particle size distribution at the lower range of particle sizes, the upper range of the x-axis was truncated to 14 nm in FIG. 4 as the y-values are essentially zero at about 13 nm and above. However, all calculations of particle sizes and statistics derived from the data shown in FIG. 4 were determined over the entire range of the distribution.

Figure 5:
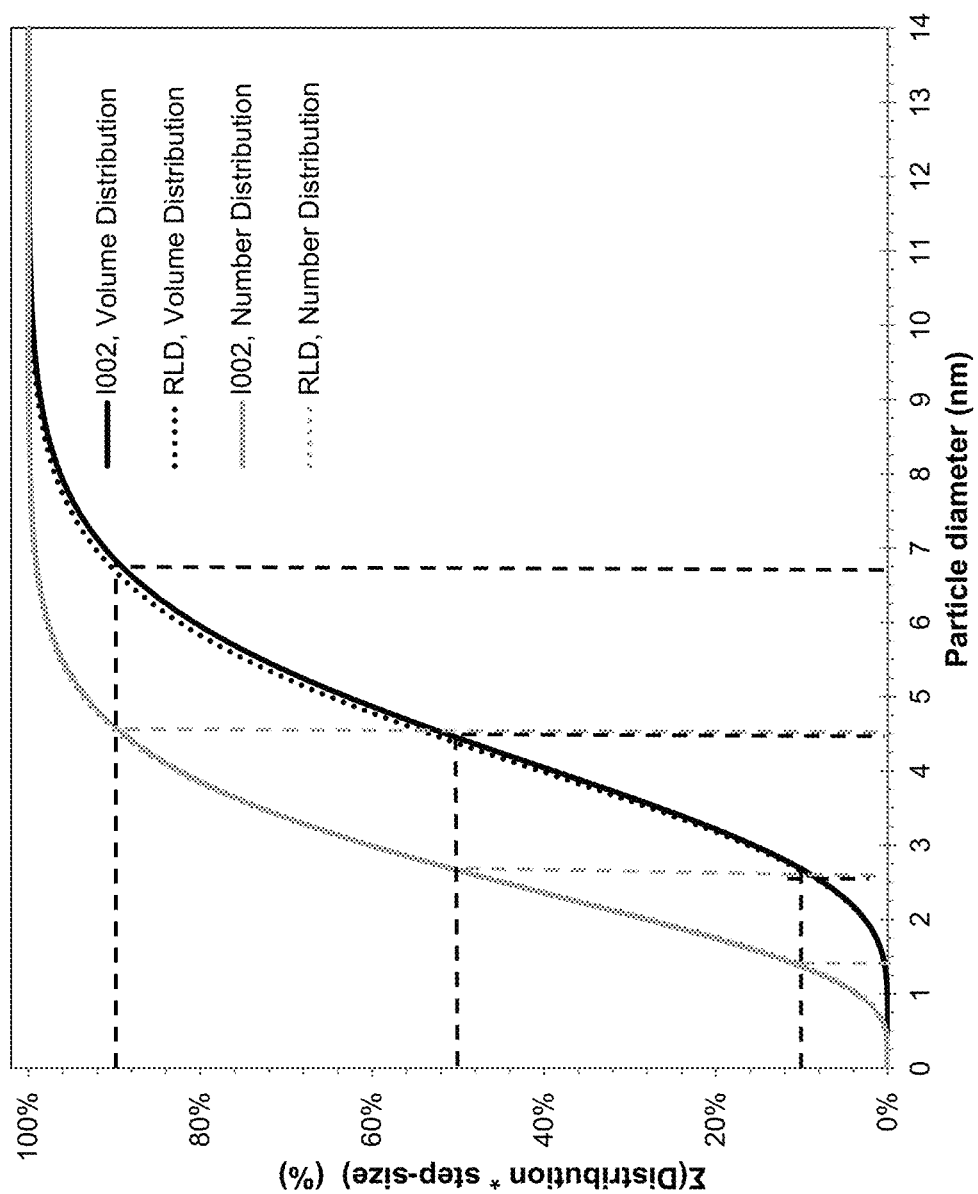
FIG. 5 is a graph illustrating the $D_{10}$, $D_{50}$, $D_{90}$ and SPAN of the particle size diameter of an iron core in iron sucrose.

For each lot of the twelve (12) lots of the iron sucrose drug product samples, the particle diameter parameters $D_x$ can be determined from the gamma distribution. FIG. 5 is a graph illustrating the $D_{10}$, $D_{50}$, $D_{90}$ and SPAN of the particle size diameter of the iron core nanoparticles in the respective iron sucrose drug product samples. The particle diameters at which 10%, 50% and 90% of the particles are smaller than (the $D_{10}$, $D_{50}$, $D_{90}$, respectively), are shown by dashed lines. In particular, FIG. 5 is a "Ydx" plot with the y-values as the cumulative sum of the gamma distribution multiplied by step-size at each x-value. The $D_x$ value is the x-value at which the y-value of the Ydx plot is x %. For example, $D_{10}$ is the x-value when the y-value is 10%, $D_{50}$ is the x-value when the y-value is 50%, and $D_{90}$ is the x-value when the y-value is 90%, as indicated by the dashed lines in the figure. From these three $D_x$ values, the SPAN can also be calculated using the formula SPAN=$(D_{90}-D_{10})/D_{50}$.

A set of evaluation equivalence criteria (EEC) can be determined based on certain parameters, such as the average particle diameter size, standard deviation of particle diameter size, $D_{10}$, $D_{50}$, $D_{90}$, and SPAN of the particle size diameter of an iron core nanoparticles in the respective iron sucrose drug product samples. In Example 1 and as shown in Table 2, the EEC is based on a range of [minimum value multiplied by (1 minus percent tolerance)] and [maximum value multiplied by (1 plus percent tolerance)], where the percent tolerance is 1000. Table 2 describes these characterization parameters in detail, and Tables 3 and 4 detail the results for these characterization parameters.

TABLE 2

Description of Characterization Parameters for Particle Diameter Size of the Iron Core Nanoparticles.

| Characterization Parameter | Description |
|---|---|
| Average Diameter (nm) | Σ (particle size * distribution * particle size interval) over the distribution |
| Standard | The standard deviation of the particle sizes, |

TABLE 2-continued

Description of Characterization Parameters for Particle Diameter Size of the Iron Core Nanoparticles.

| Characterization Parameter | Description |
|---|---|
| Deviation (nm) | determined from the product of the average diameter and relative size distribution as determined by the modeling software. |
| $D_{10}$ (nm) | Particle diameter size at which 10% of the iron core nanoparticles are smaller than this value (i.e. $\Sigma Ydx = 10\%$) |
| $D_{50}$ (nm) | Particle diameter size at which 50% of the iron core nanoparticles are smaller than this value (i.e. $\Sigma Ydx = 50\%$) |
| $D_{90}$ (nm) | Particle diameter size at which 90% of the iron core nanoparticles are smaller than this value (i.e. $\Sigma Ydx = 90\%$) |
| SPAN | $(D_{90} - D_{10}) / D50$ |
| % Tolerance | 10% |
| Min − % Tolerance | Minimum value of (COM lots) * (1 − % Tolerance) |
| Max + % Tolerance | Maximum value of (COM lots) * (1 + % Tolerance) |

TABLE 3

Observed Characterization Parameters for Particle Diameter Size of the Iron Core Nanoparticles.

| | Tested product Iron Sucrose (EQ 20 mg/ml) | | | | | | Comparison Iron Sucrose (EQ 20 mg/ml) | | | | | | Min − 10% Tolerance | Max +10% Tolerance |
|---|---|---|---|---|---|---|---|---|---|---|---|---|---|---|
| Parameter | Lot 1 | Lot 2 | Lot 3 | Lot 4 | Lot 5 | Lot 6 | Lot 1 | Lot 2 | Lot 3 | Lot 4 | Lot 5 | Lot 6 | | |
| Volume-Averaged Particle Diameter Size of the Iron Core Nanoparticles | | | | | | | | | | | | | | |
| Avg (nm) | 4.66 | 4.68 | 4.63 | 4.63 | 4.64 | 4.61 | 4.68 | 4.61 | 4.51 | 4.67 | 4.56 | 4.56 | 4.06 | 5.14 |
| SD (nm) | 1.71 | 1.62 | 1.55 | 1.69 | 1.66 | 1.64 | 1.77 | 1.62 | 1.54 | 1.65 | 1.80 | 1.61 | 1.25 | 2.23 |
| $D_{10}$ (nm) | 2.65 | 2.75 | 2.77 | 2.63 | 2.68 | 2.66 | 2.59 | 2.68 | 2.67 | 2.70 | 2.45 | 2.65 | 2.21 | 2.97 |
| $D_{50}$ (nm) | 4.45 | 4.49 | 4.45 | 4.43 | 4.44 | 4.40 | 4.45 | 4.42 | 4.33 | 4.46 | 4.32 | 4.37 | 3.89 | 4.91 |
| $D_{90}$ (nm) | 6.93 | 6.83 | 6.69 | 6.89 | 6.85 | 6.80 | 7.04 | 6.76 | 6.55 | 6.87 | 6.97 | 6.70 | 5.89 | 7.74 |
| SPAN (%) | 96 | 91 | 88 | 96 | 94 | 94 | 100 | 92 | 89 | 93 | 105 | 93 | 80 | 115 |
| Number-Averaged Particle Diameter Size of the Iron Core Nanoparticles | | | | | | | | | | | | | | |
| Avg (nm) | 2.78 | 2.99 | 3.05 | 2.78 | 2.86 | 2.85 | 2.66 | 2.89 | 2.94 | 2.91 | 2.43 | 2.86 | 2.19 | 3.23 |
| SD (nm) | 1.02 | 1.04 | 1.03 | 1.02 | 1.02 | 1.02 | 1.01 | 1.02 | 1.00 | 1.03 | 0.96 | 1.01 | 0.83 | 1.93 |
| $D_{10}$ (nm) | 1.27 | 1.50 | 1.58 | 1.29 | 1.37 | 1.37 | 1.15 | 1.41 | 1.50 | 1.41 | 0.97 | 1.39 | 0.87 | 1.65 |
| $D_{50}$ (nm) | 2.56 | 2.81 | 2.88 | 2.57 | 2.66 | 2.65 | 2.44 | 2.70 | 2.77 | 2.72 | 2.19 | 2.67 | 1.97 | 3.04 |
| $D_{90}$ (nm) | 4.54 | 4.73 | 4.74 | 4.53 | 4.60 | 4.57 | 4.45 | 4.61 | 4.59 | 4.66 | 4.19 | 4.56 | 3.77 | 5.12 |
| SPAN (%) | 128 | 115 | 110 | 126 | 122 | 121 | 136 | 118 | 112 | 119 | 147 | 119 | 101 | 162 |

TABLE 4

Tested product Compared to Comparison product with an EEC using 10% Tolerance.

| | Comparison product (from Table 3) | | Is the Tested product Iron Sucrose Drug Product (EQ 20 mg/ml) Within the EEC? | | | | | |
|---|---|---|---|---|---|---|---|---|
| Parameter | Min − 10% Tolerance | Max + 10% Tolerance | Lot 1 | Lot 2 | Lot 3 | Lot 4 | Lot 5 | Lot 6 |
| Volume-Averaged Particle Diameter Size of the Iron Core Nanoparticles | | | | | | | | |
| Avg (nm) | 4.06 | 5.14 | Yes | Yes | Yes | Yes | Yes | Yes |
| SD (nm) | 1.25 | 2.23 | Yes | Yes | Yes | Yes | Yes | Yes |
| $D_{10}$ (nm) | 2.21 | 2.97 | Yes | Yes | Yes | Yes | Yes | Yes |
| $D_{50}$ (nm) | 3.89 | 4.91 | Yes | Yes | Yes | Yes | Yes | Yes |
| $D_{90}$ (nm) | 5.89 | 7.74 | Yes | Yes | Yes | Yes | Yes | Yes |
| SPAN (%) | 80 | 115 | Yes | Yes | Yes | Yes | Yes | Yes |
| Number-Averaged Particle Diameter Size of the Iron Core Nanoparticles | | | | | | | | |
| Avg (nm) | 2.19 | 3.23 | Yes | Yes | Yes | Yes | Yes | Yes |
| SD (nm) | 0.83 | 1.93 | Yes | Yes | Yes | Yes | Yes | Yes |
| $D_{10}$ (nm) | 0.87 | 1.65 | Yes | Yes | Yes | Yes | Yes | Yes |
| $D_{50}$ (nm) | 1.97 | 3.04 | Yes | Yes | Yes | Yes | Yes | Yes |

TABLE 4-continued

Tested product Compared to Comparison product with an EEC using 10% Tolerance.

| | Source | | | | | | | |
|---|---|---|---|---|---|---|---|---|
| | Comparison product (from Table 3) | | Is the Tested product Iron Sucrose Drug Product | | | | | |
| | Min − 10% | Max + 10% | (EQ 20 mg/ml) Within the EEC? | | | | | |
| Parameter | Tolerance | Tolerance | Lot 1 | Lot 2 | Lot 3 | Lot 4 | Lot 5 | Lot 6 |
| $D_{90}$ (nm) | 3.77 | 5.12 | Yes | Yes | Yes | Yes | Yes | Yes |
| SPAN (%) | 101 | 162 | Yes | Yes | Yes | Yes | Yes | Yes |

As shown in Tables 3 and 4, the average particle diameter of the iron core nanoparticles of the comparison product RLD and tested product I002 iron sucrose drug products can be volume-averaged and number-averaged. As shown in Tables 3 and 4, an equivalent evaluation criteria (EEC) was established based on a (Min−% Tolerance) and a (Max+% Tolerance), with a 10% tolerance with respect to the RLD product. Notably, the iron core size characterization parameters for the tested product iron sucrose drug products were all within the EEC.

Example 2—Characterization of the Iron Core Nanoparticle Size in Iron Sucrose Drug Products Using Different Shape Models In Example 2, the SAXS data collected in Example 1 for lot 1 of the tested product iron sucrose drug product was re-modelled using spheroid and cylinder shape models for the iron core nanoparticles and the results compared with the sphere model of Example 1. In the cylinder model, the radius of the circular component of the cylinder is "R", the corresponding diameter is 2*R, "a" is an aspect ratio that describes the degree of elongation of the cylinder, and the length of the cylinder is 2*a*R. When a=1, the diameter of the circular component and length of the cylinder are the same. In the spheroid model, "R" is the radius of the shortest axis of the spheroid and "a" is the ratio of the radius of the longest and shortest axes. Also, a spheroid is a sphere when a=1.

Table 5 provides the results for the volume-averaged and number-averaged particle diameter size of the iron core nanoparticles and standard deviation for the three different shape models, along with an $R_{factor}$ (%) for the model. $R_{factor}$ is the sum over the entire 2-theta range of the percent disagreement between the modeled and unmodeled background-subtracted SAXS data. The similarity of the $R_{factor}$ values between the three shape models indicates all three shape models are equivalent for describing the shape of the iron core nanoparticles, with a sphere being the simplest shape model. It is noted for Table 5 that the aspect ratio of the spheroid model is the refined value from the modeling, whereas the four aspect ratios for the cylindrical model are set by the user.

TABLE 5

Different shape models for the iron core nanoparticles in iron sucrose drug products.

| | Distribution type: | | Volume-averaged particle diameter (nm) | | Number-averaged particle diameter (nm) | |
|---|---|---|---|---|---|---|
| Model shape | Aspect ratio | $R_{factor}$ (%) | Avg | SD | Avg | SD |
| Sphere | 1.00 | 5.18 | 4.66 | 1.48 | 2.78 | 1.02 |
| Spheroid | $0.88^R$ | 5.18 | 5.00 | 1.58 | 3.01 | 1.10 |
| Cylinder | $0.50^S$ | 5.15 | 5.30 | 1.34 | 4.51 | 1.22 |
| | $0.75^S$ | 5.18 | 4.49 | 1.31 | 3.53 | 1.13 |
| | $1.00^S$ | 5.18 | 4.08 | 1.20 | 3.20 | 1.03 |
| | $1.50^S$ | 5.14 | 4.49 | 1.31 | 3.01 | 1.01 |

$^R$refined parameter
$^S$parameter set by the user

Example 3—Characterization of the Iron Core Nanoparticle Size in Iron Sucrose Drug Products Using a Model with No Regular Shape (Debye Model)

In Example 3, the SAXS data collected in Example 1 for lot 1 of the tested product iron sucrose drug product was re-modelled using a Debye model, which has no regular shape. In the Debye modeling, the correlation length is defined as the length at which the probability of having a region with the same electron density at a distance 1/R away is equal to lie, and the fractal coefficient describes the degree of shape irregularity. The results in Table 6 provides a correlation length of about 2 nm and a fractal coefficient of about 0.7 for the tested product iron sucrose drug product, which are independent on the type of averaging, whether number-averaged or volume-averaged. The similarity of the $R_{factor}$ of the Debye model with that of the previously described shape models indicates it can be applied to the SAXS methods disclosed herein for characterizing particle diameter size of iron core nanoparticles in iron sucrose.

TABLE 6

Debye model of iron core nanoparticles.

| | | Volume-averaged or Number-averaged | |
|---|---|---|---|
| Model | $R_{factor}$ (%) | Correlation length (nm) | Fractal coefficient |
| Debye (no regular shape) | 5.23 | 2.06 | 0.66 |

Example 4—Characterization of the Iron Core Nanoparticles Size in Iron Sucrose Drug Products using Two or More Populations In Example 4, the SAXS data collected in Example 1 for lot 1 of the tested product iron sucrose drug product was re-modeled using two populations of spheres and the results were compared with the single population sphere model of Example 1. The results of the two-population modeling are presented in Table 7 and indicate that the average particle diameter of the iron core nanoparticles in the smaller population is about one-third that of the larger population. On a volume-averaged basis, the smaller-sized population represents about 10% of the entire population. This is reverse when the distribution is calculated on a number-averaged basis, where the smaller-sized population represents about 90% of the entire population. Although the similarity of the $R_{factor}$ for the two-population and one-population sphere models, as presented in Table 7, indicates that there is no significant benefit to modeling more than one particle population in iron sucrose; however, the two-population model can be used for development of modified iron sucrose drug product, or of similar iron carbohydrate particle drug products, whose particle population is composed of more than one populations.

2-theta angle at 0.13° and shortening the ending 2-theta angle to 7°, 6°, 5°, and so forth, and comparing the resulting data modeled with the shortened data sets with those modeled with the full-range dataset of 0.13° to 8°. In Example 5, the results were modeled using the sphere model and volume-averaging.

Figure 6B:
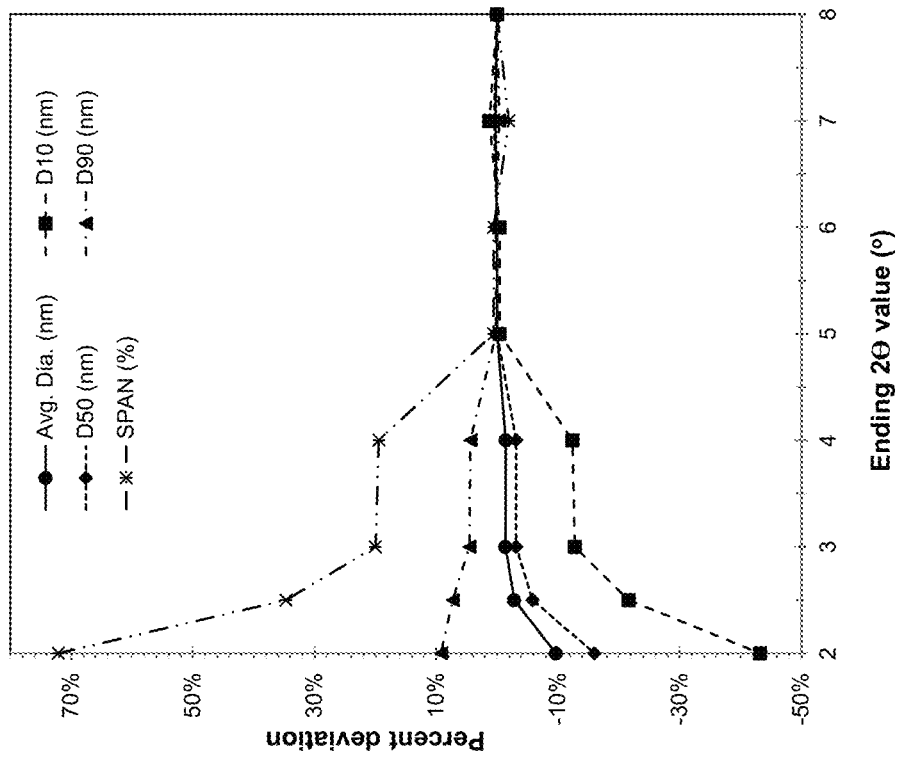
FIGS. 6A and 6B are graphs illustrating the effect of SAXS data completeness on the accuracy of the modeled particle diameter statistics.
Figure 6A:
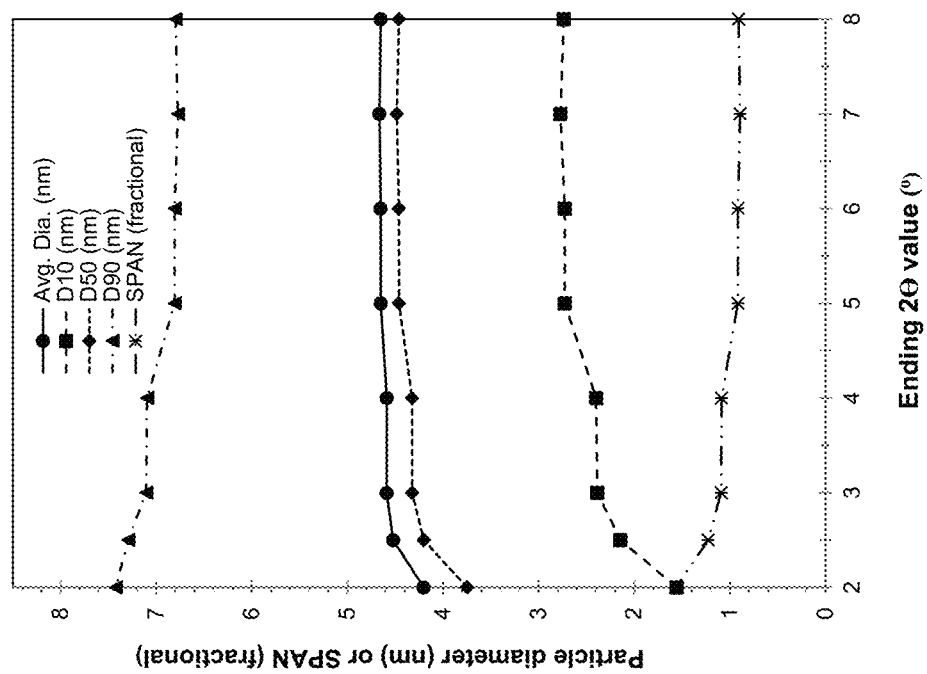

The results of this modeling trial, given in part (A) of Table 8 and graphed in FIGS. 6A-6B, shows that for a more accurate characterization of the particle diameter size of the iron core nanoparticle in iron sucrose, a complete SAXS data set needs to be collected to at least an ending 2-theta angle of 5°. FIGS. 6A-6B are graphs illustrating the effect of SAXS data completeness on the model accuracy. The ending 2-theta range from a sample SAXS full data set, 2-theta of 0.1° to 8°, was shortened to 2°, 3°, and so forth. The particle diameter data obtained from modeling of the shortened data sets were compared with those obtained from the full-range dataset of 2-theta of 0.13° to 8°. FIG. 6A is a plot of the particle diameters while FIG. 6B is the percent deviation of the shortened datasets relative to the full-range dataset. This result is more evident when the particle diameter statistics are calculated in percent deviation relative to the values obtained using the full-range of SAXS data (part (B): first column: 2-theta=0.13° to 8°). Thus, Example 5 shows that to obtain particle diameter data within 1% of the full-range

TABLE 7

Two-population sphere model of iron core nanoparticles in iron sucrose drug product.

| | | Volume-averaged particle diameter of iron core nanoparticles | | | | Number-averaged particle diameter of iron core nanoparticles | | | |
|---|---|---|---|---|---|---|---|---|---|
| No. of | $R_{factor}$ | Diameter average (nm) | | SD | Population Size | Diameter average (nm) | | SD | Population Size |
| Populations | (%) | Overall | Individual | (nm) | (%) | Overall | Individual | (nm) | (%) |
| 1 | 5.18 | 4.66 | 4.66 | 1.48 | 100 | 2.78 | 2.78 | 1.02 | 100 |
| 2 | 5.08 | 4.32 | 4.66 | 1.46 | 90 | 1.39 | 2.84 | 1.03 | 13 |
| | | | 1.18 | 0.04 | 10 | | 1.17 | 0.04 | 87 |

Example 5—Determining the Minimum Effective Ending 2-Theta Angle for SAXS for Determining Iron Core Nanoparticle Size in Iron Sucrose Drug Products In Example 5, the SAXS data collected for one lot of the tested product iron sucrose drug product, 2-theta in a range from 0.10 to 8°, was re-modeled by setting the starting data, the minimum effective ending 2-theta angle should be at least 5°. Example 5 also shows that to obtain particle diameter data within 20% of the full-range data, the minimum effective ending 2-theta angle should be at least 2.5°. It is noted that "statistics average particle diameter" and "$D_{50}$" are less sensitive than $D_{10}$ and $D_{90}$, which are more sensitive to incompleteness of the SAXS data set.

TABLE 8

Determining the minimum effective ending 2-theta angle for an accurate estimate of the particle diameter size of the iron core nanoparticles in iron sucrose by SAXS.

| | $2\Theta_{End}$ (°) | | | | | | | |
|---|---|---|---|---|---|---|---|---|
| | 8 | 7 | 6 | 5 | 4 | 3 | 2.5 | 2 |
| | PART (A) $2\Theta = 0.13°$ to different end value (volume-averaged) | | | | | | | |
| Avg. Dia. (nm) | 4.65 | 4.66 | 4.65 | 4.65 | 4.59 | 4.59 | 4.52 | 4.20 |
| $D_{10}$ (nm) | 2.74 | 2.77 | 2.73 | 2.73 | 2.40 | 2.39 | 2.15 | 1.55 |
| $D_{50}$ (nm) | 4.46 | 4.49 | 4.46 | 4.46 | 4.32 | 4.32 | 4.20 | 3.75 |
| $D_{90}$ (nm) | 6.80 | 6.77 | 6.81 | 6.81 | 7.10 | 7.11 | 7.29 | 7.42 |
| SPAN (fractional) | 0.91 | 0.89 | 0.91 | 0.91 | 1.09 | 1.09 | 1.23 | 1.57 |

TABLE 8-continued

Determining the minimum effective ending 2-theta angle for an accurate estimate of the particle diameter size of the iron core nanoparticles in iron sucrose by SAXS.

| | $2\Theta_{End}$ (°) | | | | | | | |
|---|---|---|---|---|---|---|---|---|
| | 8 | 7 | 6 | 5 | 4 | 3 | 2.5 | 2 |

| | PART (B) Percent Deviation of parameter from full-range data | | | | | | | |
|---|---|---|---|---|---|---|---|---|
| Avg. Dia. (nm) | 0.0% | 0.3% | 0.0% | 0.0% | −1.4% | −1.4% | −2.8% | −9.6% |
| $D_{10}$ (nm) | 0.0% | 1.3% | −0.4% | −0.4% | −12.4% | −12.8% | −21.6% | −43.2% |
| $D_{50}$ (nm) | 0.0% | 0.5% | 0.0% | 0.0% | −3.1% | −3.1% | −5.8% | −16.0% |
| $D_{90}$ (nm) | 0.0% | −0.3% | 0.2% | 0.2% | 4.4% | 4.6% | 7.3% | 9.2% |
| SPAN (%) | 0.0% | −1.9% | 0.6% | 0.6% | 19.4% | 20.0% | 34.7% | 72.1% |

Example 6—Determining the Minimum Effective Starting 2-Theta Angle for SAXS for Determining Iron Core Nanoparticle Size in Iron Sucrose Drug Products In Example 6, the SAXS data collected for one lot of the tested product iron sucrose drug product (2-theta of 0.1° to 8°) from Example 5, was re-modeled by setting the ending 2-theta angle at 5° and increasing the starting 2-theta angle to 0.16°, 0.19°, and so forth, and comparing the resulting statistics modeled with the shortened data sets with those modeled with the dataset from 0.13° to 5°. In Example 6, the results were modeled using the sphere model and volume-averaging.

Figure 7A:
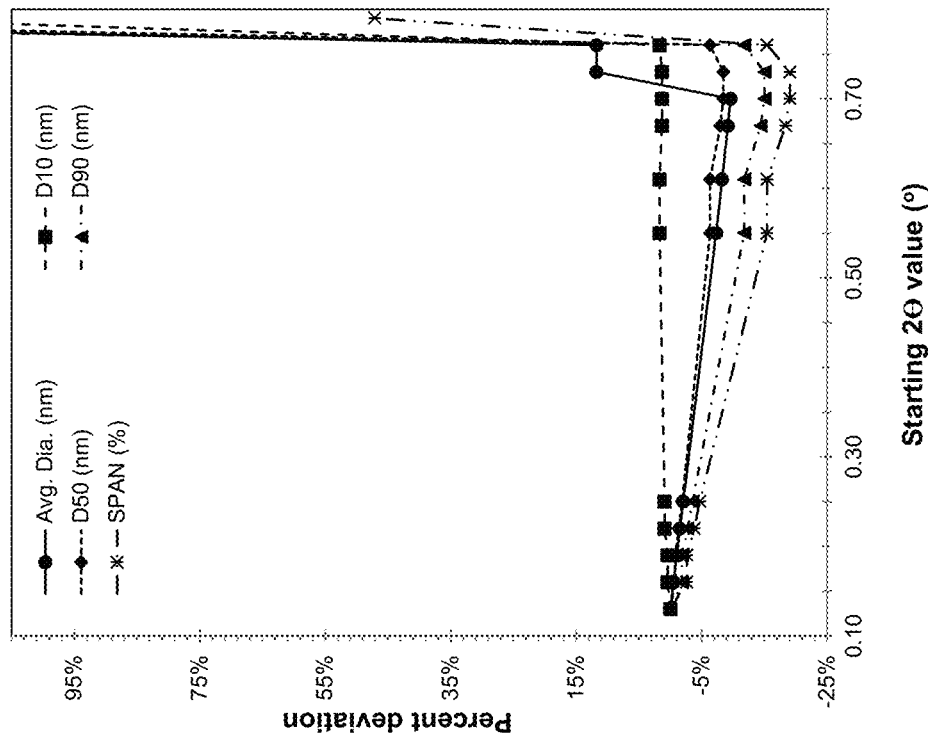
FIGS. 7A and 7B are graphs illustrating the effect of SAXS data completeness on the accuracy of the modeled particle diameter statistics.
Figure 7B:
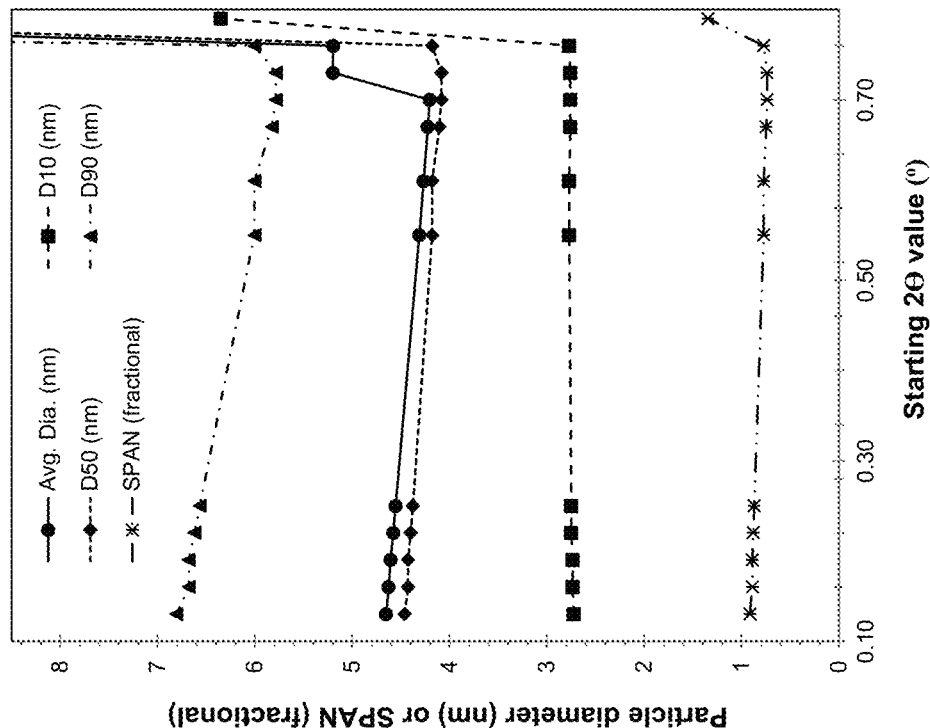

The results of this modeling trial, given in part (A) of Table 9 and graphed in FIGS. 7A-7B, show that for a more accurate characterization of the particle diameter size, a complete SAXS data set should be collected to starting 2-theta angle of about 0.2°, and ending at 2-theta angle of at least 5°. FIGS. 7A-7B are graphs illustrating the effect of SAXS data completeness on the accuracy of the modeled particle diameter data. The starting 2-theta range from a sample SAXS full data set (2-theta of 0.1° to 8°) was shortened to 0.16°, 0.19°, and so forth, and particle diameter data obtained from modeling of the shortened data sets compared with those obtained from the shortened dataset 2-theta of 0.13° to 5°. FIG. 7A is a plot of the particle diameters while FIG. 7B is the percent deviation of the shortened datasets relative to the shortened dataset 2-theta=0.13° to 5°. This result is more evident when the particle diameter data are calculated in percent deviation relative to the values obtained using the 0.13° to 5° shortened data set (part (B): first column: 2-theta=0.13° to 5°). Thus, Example 6 shows that to obtain particle diameter of the iron core nanoparticles in iron sucrose to within 1% of the full-range data, the minimum effective starting 2-theta angle should be about 0.2°. Example 6 also shows that to obtain particle diameter of the iron core nanoparticles in iron sucrose to within 5% of the full-range data, the minimum effective starting 2-theta angle should be about 0.25°. Example 6 further shows that to obtain particle diameter of the iron core nanoparticles in iron sucrose to within 15% of the full-range data, the minimum effective starting 2-theta angle should be about 0.5°. It is noted that the $D_{10}$ parameter is less sensitive to SAXS data incompleteness at low 2-theta angles than the other parameters. However, for all parameters an absolute minimum starting 2-theta angle of about 0.75° is required.

TABLE 9

Determining the effective minimum starting 2-theta angle for an accurate estimate of the particle size of iron core nanoparticles in iron sucrose drug products by SAXS.

| | $2\Theta_{End}$ (°) | | | | | | | | | | | |
|---|---|---|---|---|---|---|---|---|---|---|---|---|
| | 0.13 | 0.16 | 0.19 | 0.22 | 0.25 | 0.55 | 0.61 | 0.67 | 0.7 | 0.73 | 0.76 | 0.79 |

| | PART (A) 2Θ = different start to 2-theta of 5° (volume-averaged) | | | | | | | | | | | |
|---|---|---|---|---|---|---|---|---|---|---|---|---|
| Avg. Dia. (nm) | 4.65 | 4.63 | 4.60 | 4.58 | 4.55 | 4.31 | 4.27 | 4.23 | 4.20 | 5.20 | 5.20 | 14.61 |
| $D_{10}$ (nm) | 2.73 | 2.74 | 2.74 | 2.75 | 2.75 | 2.77 | 2.77 | 2.76 | 2.76 | 2.76 | 2.77 | 6.35 |
| $D_{50}$ (nm) | 4.46 | 4.43 | 4.43 | 4.40 | 4.38 | 4.18 | 4.18 | 4.11 | 4.08 | 4.08 | 4.18 | 13.40 |
| $D_{90}$ (nm) | 6.81 | 6.68 | 6.68 | 6.62 | 6.57 | 6.01 | 6.01 | 5.83 | 5.79 | 5.79 | 6.01 | 24.38 |
| SPAN (fractional) | 0.91 | 0.89 | 0.89 | 0.88 | 0.87 | 0.77 | 0.77 | 0.75 | 0.74 | 0.74 | 0.77 | 1.35 |

| | PART (B) Percent Deviation of parameters from 2-theta of 0.13-5° dataset | | | | | | | | | | | |
|---|---|---|---|---|---|---|---|---|---|---|---|---|
| Avg. Dia. (nm) | 0.0% | −0.6% | −1.0% | −1.6% | −2.1% | −7.3% | −8.3% | −9.2% | −9.6% | 11.8% | 11.7% | 214.0% |
| $D_{10}$ (nm) | 0.0% | 0.4% | 0.4% | 0.9% | 0.9% | 1.7% | 1.7% | 1.3% | 1.3% | 1.3% | 1.7% | 133.0% |
| $D_{50}$ (nm) | 0.0% | −0.8% | −0.8% | −1.4% | −1.9% | −6.3% | −6.3% | −8.0% | −8.5% | −8.5% | −6.3% | 200.2% |
| $D_{90}$ (nm) | 0.0% | −1.9% | −1.9% | −2.7% | −3.5% | −11.8% | −11.8% | −14.4% | −15.0% | −15.0% | −11.8% | 258.1% |
| SPAN (%) | 0.0% | −2.6% | −2.6% | −3.8% | −4.7% | −15.4% | −15.4% | −18.4% | −19.1% | −19.1% | −15.4% | 47.1% |

Example 7—Characterization of the Iron Core Nanoparticle Size in Iron Sucrose by SAXS without Background Subtraction The modeling of the SAXS intensity counts as a function of diffraction 2-theta angle in the previous six examples has been performed using background-subtracted X-ray intensity. Because the modeling of particle sizes is based on the profile (i.e., slope) of this intensity counts data, with larger particles having a profile with a larger slope, and smaller particles having a profile with a smaller slope, more accurate modeling is achieved when the measured SAXS intensity counts have been corrected to remove background intensity that is not contributed by the iron core nanoparticles. This is theoretically possible if one knows the exact buffer match to use for background subtraction. In the best scenario, this buffer should contain the same chemical composition as the iron core nanoparticles solution to be measured, except without the presence of the iron core.

FIG. 1 shows that an empty quartz capillary has a diffraction profile that is not zero because both the absorption the incident X-rays by the fused silica material of the quartz capillary, and by the X-ray system itself (i.e. X-ray optics, incident and diffracted slits, air absorption). When the background blank comprising the matched sample buffer is diffracted, a different intensity profile is observed that is due to the absorption and diffuse scattering of the SAXS by the buffer. It is this background intensity that must be subtracted from the observed raw SAXS intensity counts of the iron sucrose test samples. As shown in FIG. 1, and exemplified in Examples 5 and 6, the majority of the SAXS signal is present between 2-theta angles of about 0.2° to about 4°.

In Example 7, the effect of background diffraction on the modeled particle diameter statistics of iron sucrose drug products is examined. Example 7 analyzes the background-subtracted SAXS data for the same one lot of tested product iron sucrose drug product and one lot of RLD comparison product of Example 1, with and without subtracting the background signal from the buffer blank. In addition, one can use a similar analysis on any other nanoparticle drug products that have sufficient electron density difference between the iron core nanoparticles and blank buffer.

Figure 8:
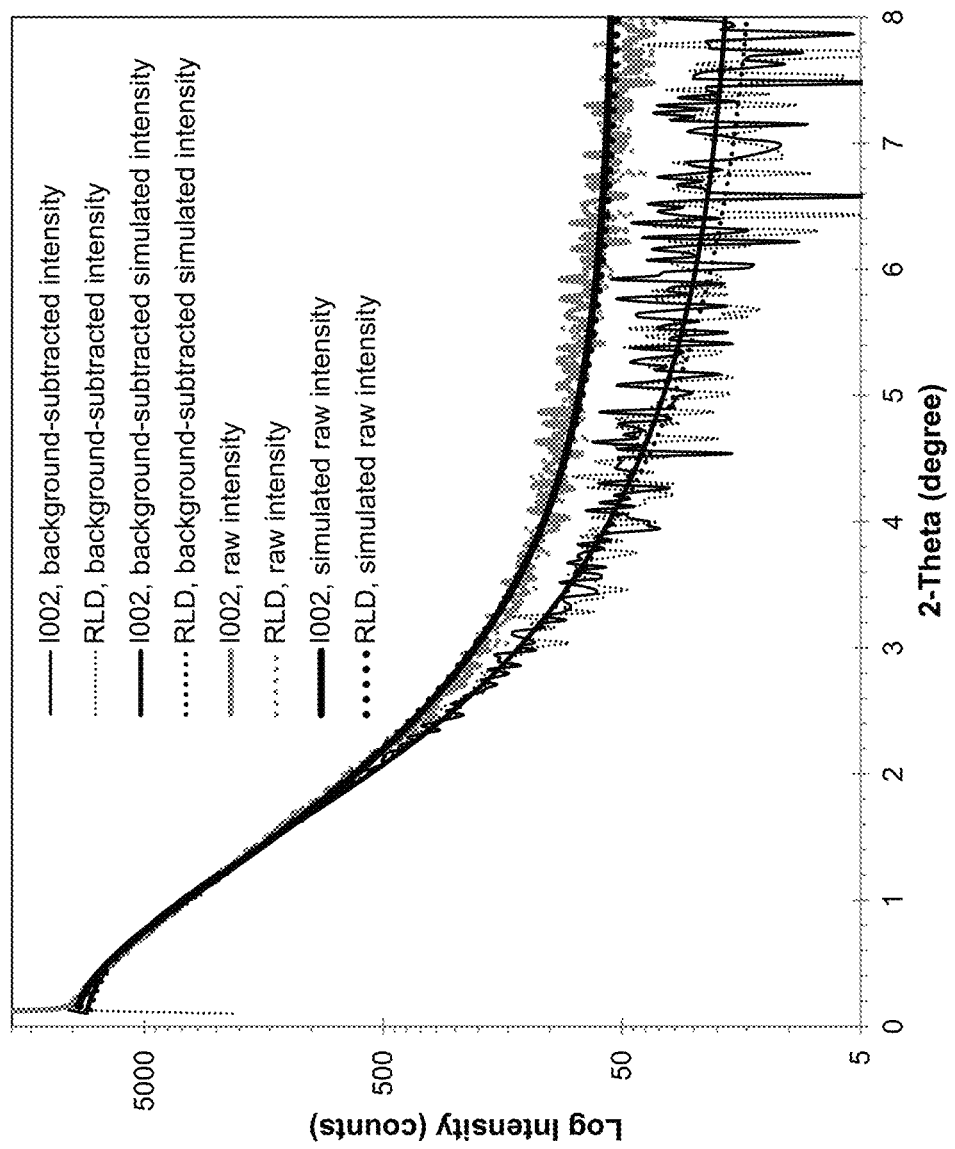
FIG. 8 is another exemplary graph showing the log intensity of the modeled and unmodeled background-subtracted scattering intensity for an iron core in iron sucrose.
Figure 9:
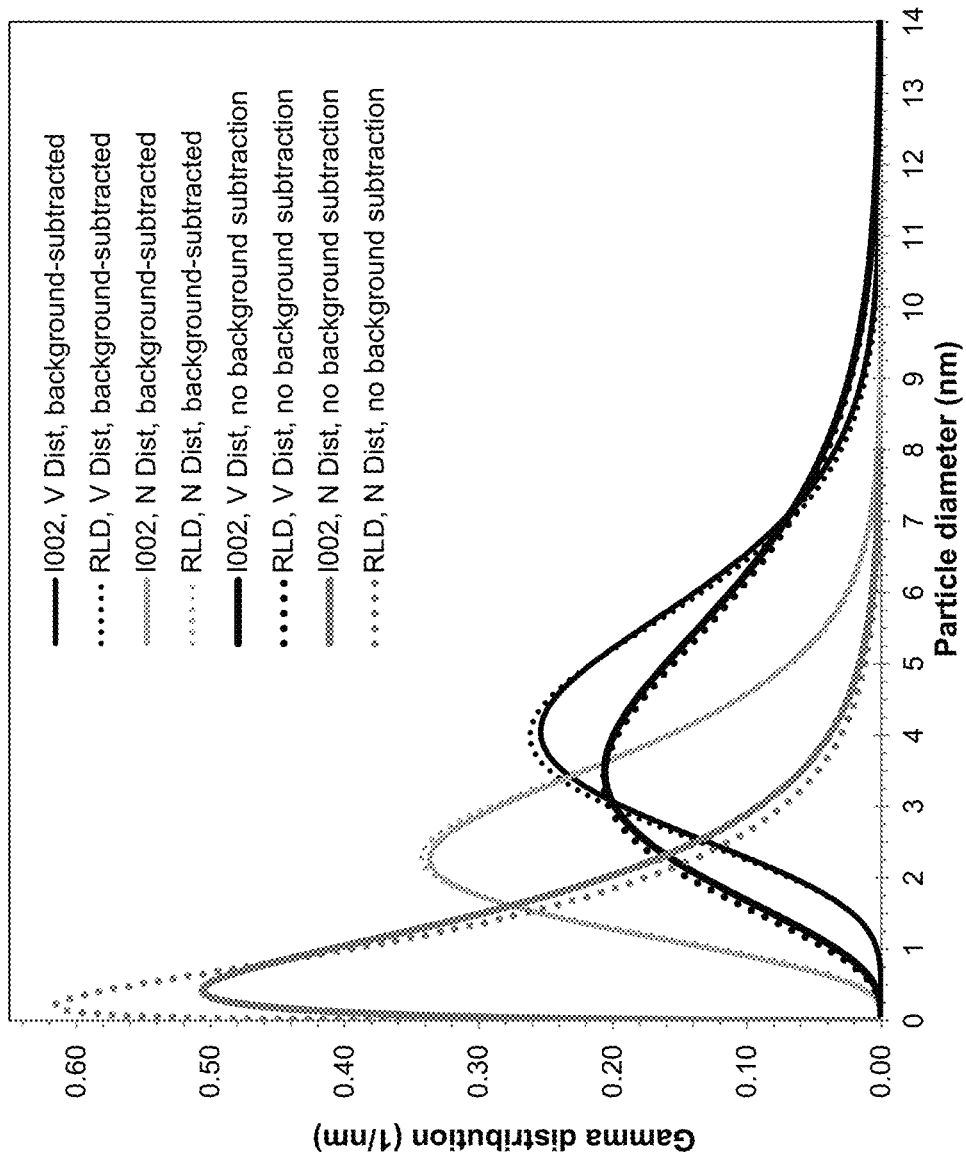
FIG. 9 is another exemplary graph illustrating the gamma distribution versus particle size diameter of an iron core in iron sucrose, shown for both volume and number-averaged calculations.
Figure 10:
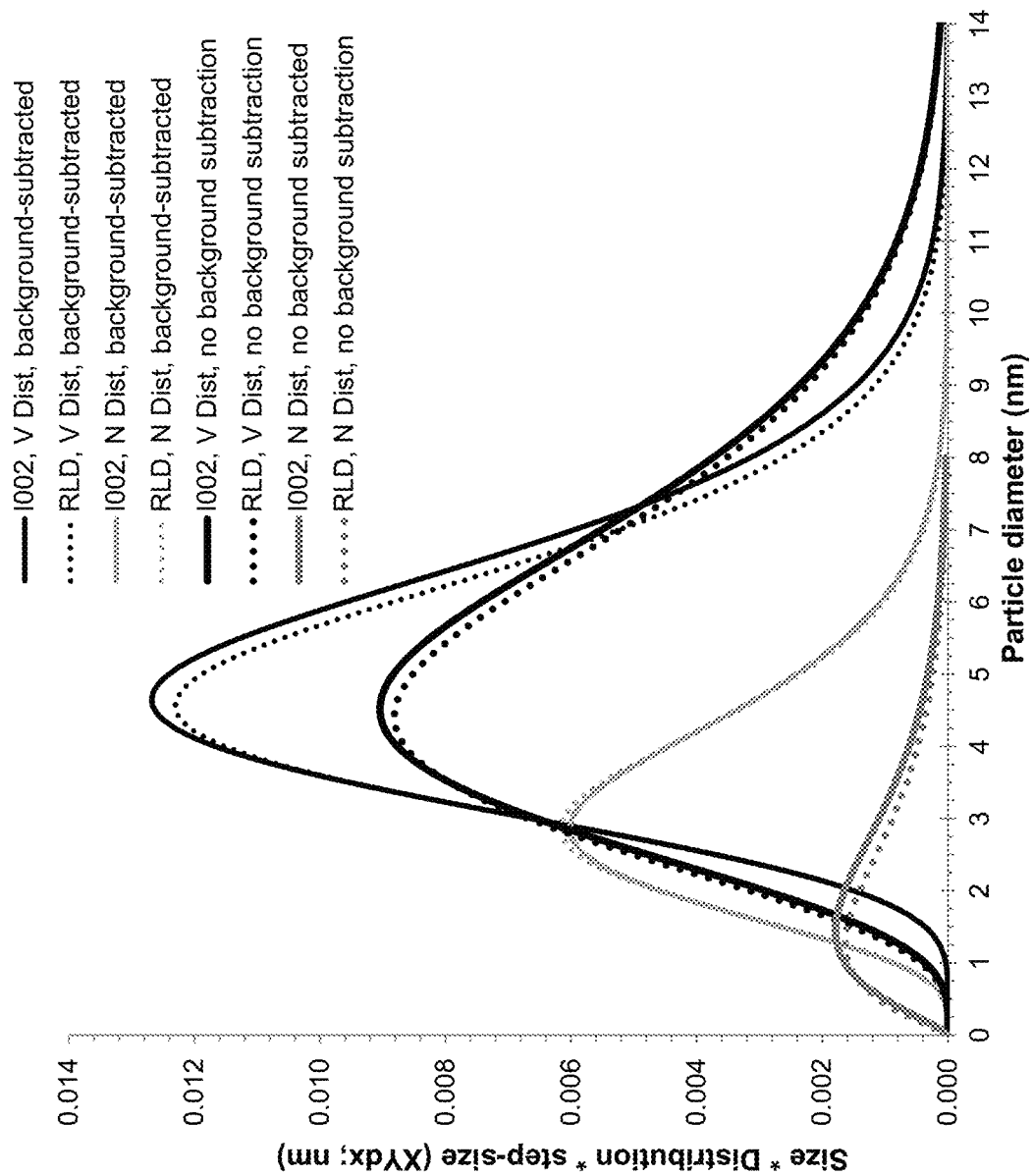
FIG. 10 is another exemplary graph illustrating the average particle size diameter of an iron core in iron sucrose. The sum of the area under the curve is the average particle size.
Figure 11:
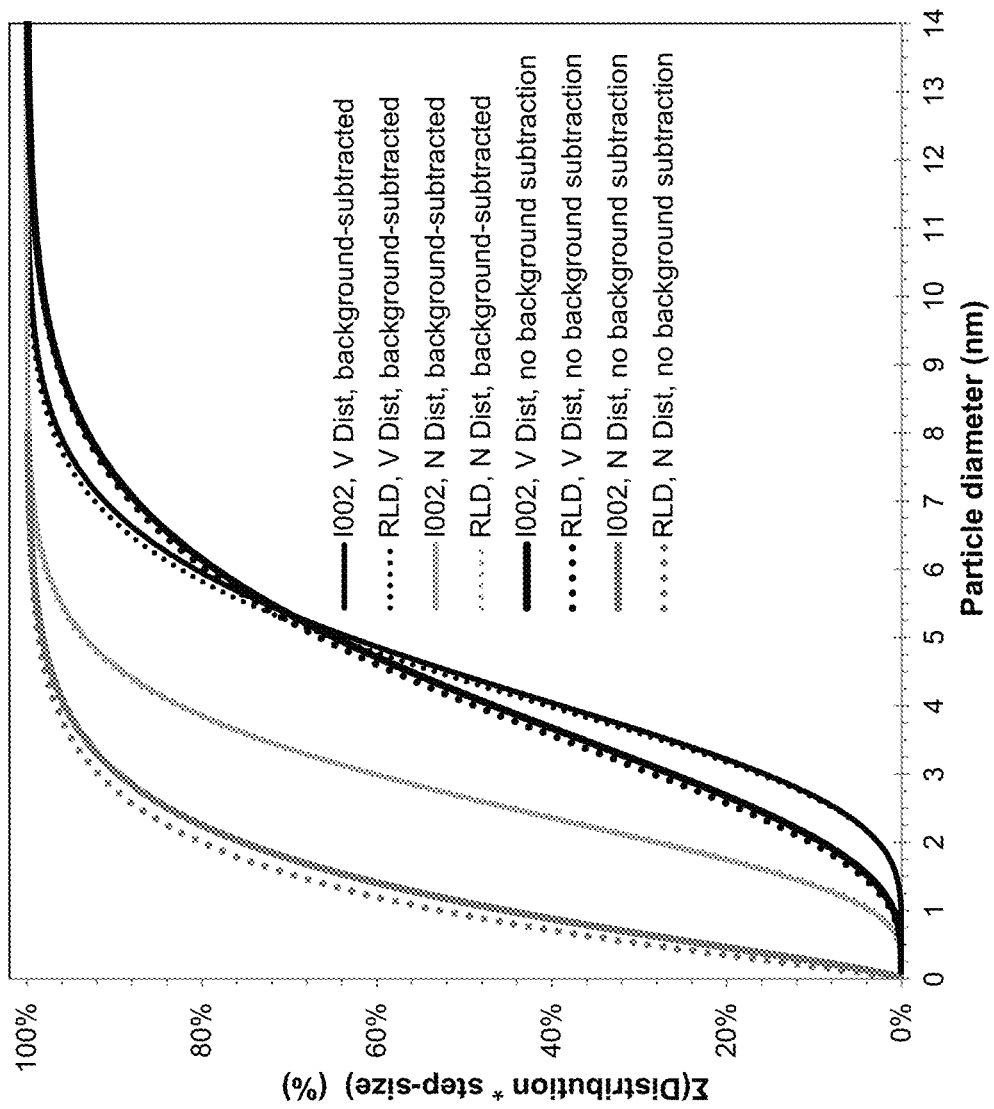
FIG. 11 is another exemplary graph illustrating the $D_{10}$, $D_{50}$, $D_{90}$ and SPAN of the particle size diameter of an iron core in iron sucrose.

FIG. 8 shows the background-subtracted and raw (i.e. not background-subtracted) SAXS intensity profile, starting from 2Θ of 0.10° (instead of 0.13°) to highlight the direct-beam noise in the measured SAXS intensity between 2Θ of 0.10° and 0.13°. This noise is likely due to the slight difference in the position of the capillary in the SAXS beam between samples. Because the noise is relatively high between 2Θ of 0.100 and 0.16°, modeling without background subtraction was performed starting from 2Θ of 0.16° instead of 0.13° for the background-subtracted case. The simulated intensity data are overlapped to show that the profiles are significantly different between the background-corrected and non-background-corrected models. FIGS. 9-11 are the corresponding particle size distribution, XYdx and Ydx plots of the background-subtracted and non-background-subtracted models. FIGS. 9-11 show that the particle sizes and particle distributions are all left-shifted (i.e. sizes are all under-estimated as smaller) when the background signal is not taken into account (e.g., not subtracted).

The results of this modeling are given in Table 10, calculated as a volume distribution of particle sizes in part (A) and as a number distribution of particle sizes in part (B). The columns labeled "% deviation" give the percent deviation of the values of the non-background corrected model from the background-corrected model. The deviations show that the volume-averaged average particle diameter size and $D_{50}$ are relatively not affected if the background signal was not corrected. However, the other volume-averaged parameters are significantly affected. When the statistics are calculated on a number-averaged basis, all statistics are under-estimated by about 50%.

TABLE 10

Effect of no background subtraction on the modeled particle diameter statistics

| | Background method: | | | | | |
|---|---|---|---|---|---|---|
| | Subtracted | | Not subtracted | | % Deviation* | |
| Parameter | 1002 | RLD | 1002 | RLD | 1002 | RLD |
| Part (A): Volume-averaged distribution of particle sizes of iron core nanoparticles | | | | | | |
| Avg. Dia. (nm) | 4.64 | 4.56 | 4.51 | 4.41 | −2.8% | −3.3% |
| $D_{10}$ (nm) | 1.66 | 1.61 | 2.15 | 2.15 | 29.2% | 33.7% |
| $D_{50}$ (nm) | 2.68 | 2.65 | 2.07 | 1.97 | −22.8% | −25.7% |
| $D_{90}$ (nm) | 4.44 | 4.37 | 4.17 | 4.06 | −6.1% | −7.1% |
| SPAN (%) | 6.85 | 6.70 | 7.38 | 7.29 | 7.7% | 8.9% |
| Avg. Dia. (nm) | 94.0% | 92.7% | 127.4% | 131.2% | 35.5% | 41.5% |
| Part (B): Number-averaged distribution of particle sizes of iron core nanoparticles | | | | | | |
| Avg. Dia. (nm) | 2.86 | 2.86 | 1.44 | 1.25 | −49.8% | −56.1% |
| $D_{10}$ (nm) | 1.02 | 1.01 | 0.68 | 0.61 | −33.2% | −39.4% |
| $D_{50}$ (nm) | 1.37 | 1.39 | 0.26 | 0.18 | −81.0% | −87.0% |
| $D_{90}$ (nm) | 2.66 | 2.67 | 1.12 | 0.93 | −57.9% | −65.1% |
| SPAN (%) | 4.60 | 4.56 | 3.06 | 2.78 | −33.6% | −39.1% |
| Avg. Dia. (nm) | 121.6% | 118.9% | 249.6% | 278.5% | 105.3% | 134.3% |

*(Parameter$_{Not-background\ subtracted}$ − Parameter$_{Background-subtracted}$) / Parameter$_{Background-subtracted}$ While the invention has been described and illustrated herein by references to various specific materials, procedures, and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

We claim:

1. A method for rapidly characterizing the iron core of iron carbohydrate colloid nanoparticle products comprising the steps of:
configuring an X-ray diffractometer in a parallel beam transmission geometry for small-angle X-ray scattering (SAXS);
performing SAXS data collection on a first sample of the iron core carbohydrate colloid product as it exists in solution, such sample having been un-manipulated so as to not perturb the iron core and mounted in a capillary; such data being collected from a 2-theta scattering angle of about 0.1° to about 8° in 0.03° increments;
performing SAXS with identical instrument settings on a second solution sample comprising the same or approximately the same carbohydrate composition as the first sample, but without iron;
performing background subtraction of the X-ray intensities as a function of 2-theta scattering angle by subtracting the X-ray intensities of the second sample from the first sample;
generating a modeled background-subtracted SAXS data by modelling the background-subtracted X-ray intensities as a function of 2-theta scattering angle by fitting a distribution(s) of solid iron core particles of different shapes and sizes; such sizes ranging from 0 nm to about 20 nm; such modelling being performed without requiring a priori information or knowledge of the iron core's sub-structure; outputting the size distribution(s), such distribution(s) having a characteristic average particle diameter(s) and relative size distribution(s); and
calculating the volume-averaged or number-averaged average particle diameter(s) and other size parameters from the size distribution(s).

2. The method of claim 1, wherein the size distribution(s) is a Gamma distribution or Lognormal distribution of different particle sizes.

3. The method of claim 1, wherein the shape is a solid sphere, a solid spheroid, a solid cylinder, a spherical core shell, or a Debye particle of unspecified shape.

4. The method of claim 1, wherein the SAXS data is separately collected with identical instrument settings on two different first samples of the same type of colloidal iron core carbohydrate product; the background SAXS signal from the second sample are then subtracted from their individual SAXS signals; modelling of the individual background-subtracted X-ray intensities are performed identically; and the average particle diameters and other size parameters calculated from the size distribution(s) are used for comparing the measured properties of their iron cores.

5. The method of claim 1, wherein the iron core carbohydrate colloid product is iron sucrose, iron dextran, sodium ferric gluconate, iron carboxymaltose, or ferumoxytol.

6. The method of claim 1, wherein the pre-determined range of scattering angles is:
a range, in 2-theta (2Θ), from about 0.1 degrees to about 8 degrees;
a range, in 2-theta (2Θ), from about 0.1 degrees to about 5 degrees;
a range, in 2-theta (2Θ), from about 0.2 degrees to about 8 degrees; or
a range, in 2-theta (2Θ), from about 0.2 degrees to about 5 degrees.

7. The method of claim 1, wherein the particle size parameter $D_x$ includes a $D_{10}$, a $D_{50}$, and a $D_{90}$, wherein:
$D_{10}$ is a particle diameter size of the iron core nanoparticles in the respective sample in which 10% of the iron core nanoparticles have a particle diameter size less than the $D_{10}$;
$D_{50}$ is a particle diameter size of the iron core nanoparticles in the respective sample in which 50% of the iron core nanoparticles have a particle diameter size less than the $D_{50}$ and 50% of the iron core nanoparticles have a particle diameter size more than the $D_{50}$; and
$D_{90}$ is a particle diameter size of the iron core nanoparticles in the respective sample in which 90% of the iron core nanoparticles have a particle diameter size less than the $D_{90}$, and optionally wherein the method further comprises the step of determining a SPAN value based on the formula $SPAN=(D_{90}-D_{10})/D_{50}$.

8. A method for characterizing an average particle diameter size of iron core nanoparticles in an iron carbohydrate drug product comprising the steps of:
configuring an X-ray diffractometer in a parallel beam transmission geometry for small-angle X-ray scattering (SAXS);
performing SAXS on a first sample having a plurality of iron carbohydrate particles to generate a first SAXS data, wherein the SAXS data includes intensity counts as a function of scattering angle, wherein each iron carbohydrate particle exhibits a colloidal system comprising an iron core nanoparticle and a plurality of carbohydrate nanoparticles surrounding the iron core nanoparticle, and wherein the SAXS is performed over a pre-determined range of scattering angles;
performing SAXS with identical instrument settings over the pre-determined range of scattering angles on a second sample comprising the same composition as the first sample but without iron to generate a second SAXS data;
generating a first background-subtracted SAXS data by subtracting the second SAXS data from the first SAXS data, wherein the background-subtracted SAXS data includes background-subtracted intensity counts as a function of scattering angle;
generating a first modeled background-subtracted SAXS data by modeling the first background-subtracted SAXS data as a Gamma or Lognormal distribution(s) of particles of different sizes using a projected shape of the iron core nanoparticle and a projected particle diameter size of the iron core nanoparticle; such distribution(s) having a characteristic average particle diameter size and relative size distribution of the iron core nanoparticle; and
determining a first average particle diameter size(s) and other diameter parameters of the iron core nanoparticles in the plurality of iron carbohydrate particles of the first sample based on the first size distribution(s).

9. A method for characterizing an average particle diameter size of iron core nanoparticles in an iron carbohydrate drug product comprising the steps of:
configuring an X-ray diffractometer in a parallel beam transmission geometry for SAXS;
performing SAXS on a first sample having a plurality of iron carbohydrate particles to generate a first SAXS data, wherein the SAXS data includes intensity counts as a function of scattering angle, wherein each iron carbohydrate particle exhibits a colloidal system comprising an iron core nanoparticle and a plurality of carbohydrate nanoparticles surrounding the iron core nanoparticle, and wherein the SAXS is performed over a pre-determined range of scattering angles;
performing SAXS with identical instrument settings over the pre-determined range of scattering angles on a second sample comprising the same composition as the first sample but without no iron to generate a second SAXS data;
generating a first background-subtracted SAXS data by subtracting the second SAXS data from the first SAXS data, wherein the background-subtracted SAXS data includes background-subtracted intensity counts as a function of scattering angle;
generating a first modeled background-subtracted SAXS data by modeling the first background-subtracted SAXS data as a Gamma or Lognormal distribution(s) of particles of different sizes using a projected shape of the iron core nanoparticle and a projected particle diameter size of the iron core nanoparticle; such distribution(s) having a characteristic average particle diameter size and relative size distribution of the iron core nanoparticle;
performing SAXS with identical instrument settings over the pre-determined range of scattering angles on a third sample having a plurality of iron carbohydrate particles to generate a third SAXS data;
generating a second background-subtracted SAXS data by subtracting the second SAXS data from the third SAXS data;
generating a second modeled background-subtracted SAXS data by modeling the second background-subtracted SAXS data as a Gamma or Lognormal distribution(s) of particles of different sizes using the projected shape of the iron core nanoparticle and the projected particle diameter size of the iron core nanoparticle; such distribution(s) having a characteristic average particle diameter size and relative size distribution of the iron core nanoparticle; and
determining a first average particle diameter size(s) and other diameter parameters of the iron core nanoparticles in the plurality of iron carbohydrate particles of the first sample based on the first size distribution(s); and
determining a second average particle diameter size(s) and other diameter parameters of the iron core nanoparticles in the plurality of iron sucrose particles of the third sample based on the second size distribution(s),
wherein the first sample is a test iron carbohydrate drug product and the third sample is a comparison drug product for the iron carbohydrate, and
wherein when first average particle diameter size(s) and the second average particle diameter size(s) are same or substantially the same the test iron carbohydrate drug product is structurally similar to the comparison product.

10. A method for characterizing an average particle diameter size of iron core nanoparticles in iron sucrose comprising the steps of:
configuring an X-ray diffractometer in a parallel beam transmission geometry for SAXS;
performing SAXS on a first sample having a plurality of iron sucrose particles to generate a first SAXS data, wherein the SAXS data includes intensity counts as a function of scattering angle, wherein each iron sucrose particle exhibits a colloidal system comprising an iron core nanoparticle and a plurality of sucrose nanoparticles surrounding the iron core nanoparticle, and wherein the SAXS is performed over a pre-determined range of scattering angles;
performing SAXS with identical instrument settings over the pre-determined range of scattering angles on a second sample comprising the same composition as the first sample but without iron to generate a second SAXS data;
generating a first background-subtracted SAXS data by subtracting the second SAXS data from the first SAXS data, wherein the background-subtracted SAXS data includes background-subtracted intensity counts as a function of scattering angle;
generating a first modeled background-subtracted SAXS data by modeling the first background-subtracted SAXS data as a Gamma or Lognormal distribution(s) of particles of different sizes using a projected shape of the iron core nanoparticle and a projected particle diameter size of the iron core nanoparticle; such distribution(s) having a characteristic average particle diameter size and relative size distribution of the iron core nanoparticle; and
determining a first average particle diameter size(s) and other diameter parameters of the iron core nanoparticles in the plurality of iron sucrose particles of the first sample based on the first size distribution(s).

11. A method of determining structural similarity between a test iron sucrose product and a comparison drug product for iron sucrose based characterizing average particle diameter size of iron core nanoparticles in iron sucrose comprising the steps of:
configuring an X-ray diffractometer in a parallel beam transmission geometry for SAXS;
performing SAXS on a first sample having a plurality of iron sucrose particles to generate a first SAXS data, wherein the SAXS data includes intensity counts as a function of scattering angle, wherein each iron sucrose particle exhibits a colloidal system comprising an iron core nanoparticle and a plurality of sucrose nanoparticles surrounding the iron core nanoparticle, and wherein the SAXS is performed over a pre-determined range of scattering angles;
performing SAXS with identical instrument settings over the pre-determined range of scattering angles on a second sample comprising the same composition as the first sample but without iron to generate a second SAXS data;
generating a first background-subtracted SAXS data by subtracting the second SAXS data from the first SAXS data, wherein the background-subtracted SAXS data includes background-subtracted intensity counts as a function of scattering angle;
generating a first modeled background-subtracted SAXS data by modeling the first background-subtracted SAXS data as a Gamma or Lognormal distribution(s) of particles of different sizes using a projected shape of the iron core nanoparticle and a projected particle diameter size of the iron core nanoparticle; such distribution(s) having a characteristic average particle diameter size and relative size distribution of the iron core nanoparticle;

performing SAXS with identical instrument settings over the pre-determined range of scattering angles on a third sample having a plurality of iron sucrose particles to generate a third SAXS data;

generating a second background-subtracted SAXS data by subtracting the second SAXS data from the third SAXS data;

generating a second modeled background-subtracted SAXS data by modeling the second background-subtracted SAXS data as a Gamma or Lognormal distribution(s) of particles of different sizes using the projected shape of the iron core nanoparticle and the projected particle diameter size of the iron core nanoparticle; such distribution(s) having a characteristic average particle diameter size and relative size distribution of the iron core nanoparticle;

determining a first average particle diameter size(s) and other diameter parameters of the iron core nanoparticles in the plurality of iron sucrose particles of the first sample based on the first size distribution(s); and determining a second average particle diameter size(s) and other diameter parameters of the iron core nanoparticles in the plurality of iron sucrose particles of the third sample based on the second size distribution(s);

wherein the first sample is a test iron sucrose drug product and the third sample is a comparison drug product for iron sucrose; and wherein when first average particle diameter size(s) and the second average particle diameter size(s) are same or substantially the same the test iron sucrose drug product is structurally similar to the comparison drug product.

12. The method of claim 9, wherein the determined first and second average particle diameter sizes of the iron core nanoparticles are based on volume-averaged particle diameter sizes or a on numbered-averaged particle diameter sizes, wherein the distribution data is based on a volume-averaging of the particle diameter sizes of the iron core nanoparticles when the average particle diameter sizes of the iron core nanoparticles are based on volume-averaged particle diameter sizes, and wherein the distribution data is based on a number-averaging of the particle diameter sizes of the iron core nanoparticles when the particle diameter sizes of the iron core nanoparticles is based on numbered-averaged particle diameter sizes.

13. The method of claim 12, wherein there is one gamma distribution, and wherein the projected particle diameter size of the iron core nanoparticle is about 1 nm to about 3 nm, about 4 nm to about 6 nm volume-averaged, about 2 nm numbered-averaged or about 5 nm volume-averaged.

14. The method of claim 8, wherein the projected shape of the iron core nanoparticle is selected from the group consisting of a sphere, a spheroid, a cylinder, a core-shell, and a Debye particle of undefined shape.

15. The method of claim 8, wherein the pre-determined range of scattering angles is:
a range, in 2-theta (2Θ), from about 0.1 degrees to about 8 degrees;
a range, in 2-theta (2Θ), from about 0.1 degrees to about 5 degrees;
a range, in 2-theta (2Θ), from about 0.2 degrees to about 8 degrees; or
a range, in 2-theta (2Θ), from about 0.2 degrees to about 5 degrees.

16. The method of claim 9, further comprising the steps of: determining a set of equivalence evaluation criteria (EEC), wherein the set of EEC comprises at least one EEC based on the second average particle diameter size of the iron core nanoparticles; and each EEC is based on a range of
minimum value x(1−% tolerance)
and
maximum value x(1+% tolerance)
and
determining whether the first average particle diameter size of the iron core nanoparticles meets.

17. The method of claim 9, wherein the particle diameter parameters include:
determining a first set of one or more $D_x$ based on the first gamma distribution data; and
determining a second set of one or more $D_x$ based on the second gamma distribution data;
wherein the $D_x$ is a particle diameter size of the iron core nanoparticles in the respective sample in which x % of the iron core nanoparticles have a particle diameter size less than the $D_x$, and optionally wherein the one or more $D_x$ includes a $D_{10}$, a $D_{50}$, and a $D_{90}$, wherein:
the $D_{10}$ is a particle diameter size of the iron core nanoparticles in the respective sample in which 10% of the iron core nanoparticles have a particle diameter size less than the $D_{10}$;
the $D_{50}$ is a particle diameter size of the iron core nanoparticles in the respective sample in which 50% of the iron core nanoparticles have a particle diameter size less than the $D_{50}$ and 50% of the iron core nanoparticles have a particle diameter size more than the $D_{50}$; and
the $D_{90}$ is a particle diameter size of the iron core nanoparticles in the respective sample in which 90% of the iron core nanoparticles have a particle diameter size less than the $D_{90}$.

18. The method of claim 17, further comprising the step of:
determining a first SPAN based on the first set of $D_x$; and
determining a second SPAN based on the second set of $D_x$; wherein the SPAN is determined based on $(D_{90}-D_{10})/D_{50}$.

19. The method of claim 17, further comprising the steps of:
determining a set of equivalence evaluation criteria (EEC), wherein the set of EEC comprises at least four EECs based on the second average particle diameter size of the iron core nanoparticles and the second set of $D_x$, and each EEC is based on a range of [minimum value multiplied by (1 minus percent tolerance)] and [maximum value multiplied by (1 plus percent tolerance)]; and
determining whether the first average particle diameter size of the iron core nanoparticles and the first set of $D_x$ meets the corresponding EEC in the set of EEC.

20. The method of claim 19, wherein the first and second set of $D_x$ includes the $D_{10}$, the $D_{50}$, and the $D_{90}$ and/or wherein the set of EEC further includes the SPAN, wherein the SPAN is determined based on $(D_{90}-D_{10})/D_{50}$.

21. The method of claim 9, further comprising the steps of: determining a set of equivalence evaluation criteria (EEC), wherein the set of EEC comprises at least one EEC based on the second average particle diameter size of the iron core nanoparticles; and each EEC is determined based on one or more of the following EEC Equations with n=10%;

$$\text{EEC Lower Limit} = R_{min} * (1-\eta) \quad (1)$$

$$\text{EEC Upper Limit} = R_{max} * (1+\eta) \quad (2)$$

and determining whether the first average particle diameter of the iron core nanoparticles size meets the EEC.

22. The method of claim 9, wherein the plurality of sucrose nanoparticles: serves as a ligand to the iron core nanoparticle; surrounds the iron core nanoparticle by forming a shell of sucrose nanoparticles around the iron core nanoparticle; and/or the plurality of sucrose particle is up to about 50 sucrose particles.

23. The method of claim 8, wherein the SAXS uses a wavelength of about 0.14 nm to about 0.16 nm or about 0.15 nm.

24. The method of claim 9, wherein the tested iron sucrose product and the comparison drug product for iron sucrose both have an equivalent concentration of about 20 mg/mL of iron.

\* \* \* \* \*